(12) United States Patent
Pawluczyk et al.

(10) Patent No.: US 12,162,042 B2
(45) Date of Patent: Dec. 10, 2024

(54) DEVICES, SYSTEMS AND METHODS FOR SORTING AND LABELLING FOOD PRODUCTS

(71) Applicant: P&P OPTICA INC., Waterloo (CA)

(72) Inventors: Romuald Pawluczyk, Conestogo (CA);
Olga Ewa Pawluczyk, Waterloo (CA);
Timothy M. F. Stork, Kitchener (CA);
Allan Hamzic, Kitchener (CN);
Bradley Oldenburg, Waterloo (CA)

(73) Assignee: P & P OPTICA INC., Waterloo (CA)

( * ) Notice: Subject to any disclaimer, the term of this patent is extended or adjusted under 35 U.S.C. 154(b) by 210 days.

(21) Appl. No.: 17/635,961

(22) PCT Filed: Aug. 20, 2019

(86) PCT No.: PCT/IB2019/057019
§ 371 (c)(1),
(2) Date: Feb. 16, 2022

(87) PCT Pub. No.: WO2021/033012
PCT Pub. Date: Feb. 25, 2021

(65) Prior Publication Data
US 2022/0323997 A1 Oct. 13, 2022

(51) Int. Cl.
*B07C 5/342* (2006.01)
*G01N 21/17* (2006.01)
(Continued)

(52) U.S. Cl.
CPC ......... *B07C 5/3422* (2013.01); *G01N 21/31* (2013.01); *G01N 21/84* (2013.01); *G01N 33/12* (2013.01);
(Continued)

(58) Field of Classification Search
CPC . B07C 5/3422; B07C 2501/0081; B07C 5/34; G01N 21/31; G01N 21/84;
(Continued)

(56) References Cited

U.S. PATENT DOCUMENTS

| | | | |
|---|---|---|---|
| 5,887,073 A * | 3/1999 | Fazzari | B07C 5/3422 382/110 |
| 6,864,970 B1 * | 3/2005 | Ruymen | B07C 5/342 356/237.1 |

(Continued)

FOREIGN PATENT DOCUMENTS

JP 5103736 B2 12/2012

OTHER PUBLICATIONS

Barbon Jr., et al, "Machine Learning Applied to Near-Infrared Spectra for Chicken Meat Classification", Journal of Spectroscopy, vol. 2018, Article ID 8949741, Aug. 7, 2018.

(Continued)

*Primary Examiner* — Tarifur R Chowdhury
*Assistant Examiner* — Akbar H. Rizvi
(74) *Attorney, Agent, or Firm* — PERRY + CURRIER, INC.

(57) ABSTRACT

Devices, systems and methods for sorting and labeling food products are provided. Respective spectra of food products for a plurality of segments of a line are received at a controller from at least one line-scan dispersive spectrometer configured to acquire respective spectra of the food products for the plurality of segments of the line. The controller applies one or more machine learning algorithms to the respective spectra to classify the plurality of segments according to at least one of one or more food parameters. The controller controls one or more of a sorting device and a labeling device according to classifying the plurality of segments to cause the food products to be one or more of (Continued)

sorted and labeled according to the at least one of the one or more food parameters.

20 Claims, 16 Drawing Sheets

(51) Int. Cl.
    *G01N 21/31*     (2006.01)
    *G01N 21/84*     (2006.01)
    *G01N 33/12*     (2006.01)

(52) U.S. Cl.
    CPC ............. *B07C 2501/0081* (2013.01); *G01N 2021/1774* (2013.01); *G01N 2021/845* (2013.01); *G01N 2201/0438* (2013.01); *G01N 2201/121* (2013.01); *G01N 2201/12792* (2013.01)

(58) Field of Classification Search
    CPC ........... G01N 33/12; G01N 2021/1774; G01N 2021/845; G01N 2201/0438; G01N 2201/121; G01N 2201/12792; G01N 2021/8883; G01N 33/02; G01N 2201/129; G01N 21/94; G06N 5/01; G06N 7/01; G06N 20/20; G06N 3/045; G06N 20/10; G16C 20/20; G16C 20/70
    See application file for complete search history.

(56) References Cited

U.S. PATENT DOCUMENTS

| | | | | |
|---|---|---|---|---|
| 10,323,983 | B1* | 6/2019 | Iyer | ........................ G01J 3/0202 |
| 2008/0024778 | A1* | 1/2008 | Honda | ................... G01N 21/85 |
| | | | | 702/22 |
| 2008/0253648 | A1 | 10/2008 | Mulder et al. | |
| 2014/0268136 | A1* | 9/2014 | Pawluczyk | ............ H04N 25/68 |
| | | | | 356/326 |
| 2015/0290684 | A1* | 10/2015 | Cadieux, Jr. | ........... G01N 21/94 |
| | | | | 209/587 |
| 2018/0056334 | A1* | 3/2018 | Justice | .................. B07C 5/3425 |
| 2018/0136451 | A1* | 5/2018 | Soenksen | ............... H04N 7/183 |
| 2019/0204577 | A1* | 7/2019 | Faris | .................. G02B 21/0088 |

OTHER PUBLICATIONS

Du et al., "Learning Techniques Used in Computer Vision for Food Quality Evaluation: a Review", Journal of Food Engineering, 72 pp. 39-55, Jan. 5, 2005, pp. 41, 42, table 1.

"International Search Report", mailed Apr. 22, 2020, issued in corresponding PCT Application No. PCT/IB2019/057019, Filed Aug. 20, 2019.

Kim, M S.,"Online screening of fruits and vegetables using hyperspectral line-scan imaging techniques." High Throughput Screening for Food Safety Assessment. Woodhead Publishing, 2015. 467-490.

Chen, Yud-Ren et al., "Machine vision technology for agricultural applications." Computers and electronics in Agriculture 36.2-3 (2002): 173-191.

Wu, Di, et al."Advanced Applications of Hyperspectral Imaging Technology for Food Quality and Safety Analysis and Assessment: A Review—Part I: Fundamentals." Innovative Food Science & Emerging Technologies, vol. 19, Jul. 1, 2013, pp. 1-14.

Ravikanth, Lankapalli et al., "Extraction of Spectral Information From Hyperspectral Data and Application of Hyperspectral Imaging for Food and Agricultural Products", Food and Bioprocess Technology; An International Journal, Springer-Verlag, New York, vol. 10, No. 1, 2017, pp. 1-33.

* cited by examiner

DEVICES, SYSTEMS AND METHODS FOR SORTING AND LABELLING FOOD PRODUCTS

BACKGROUND

Imaging of food products to determine quality, and the like, may be challenging. In some approaches, cameras acquire images of food products being conveyed (e.g. in a factory) using a conveyor. However, simple camera images of the food products may not yield enough information to accurately determine quality of the food products, even when machine learning algorithms are used to classify the camera images.

BRIEF DESCRIPTIONS OF THE DRAWINGS

For a better understanding of the various examples described herein and to show more clearly how they may be carried into effect, reference will now be made, by way of example only, to the accompanying drawings in which.

DETAILED DESCRIPTION

Figure 1:
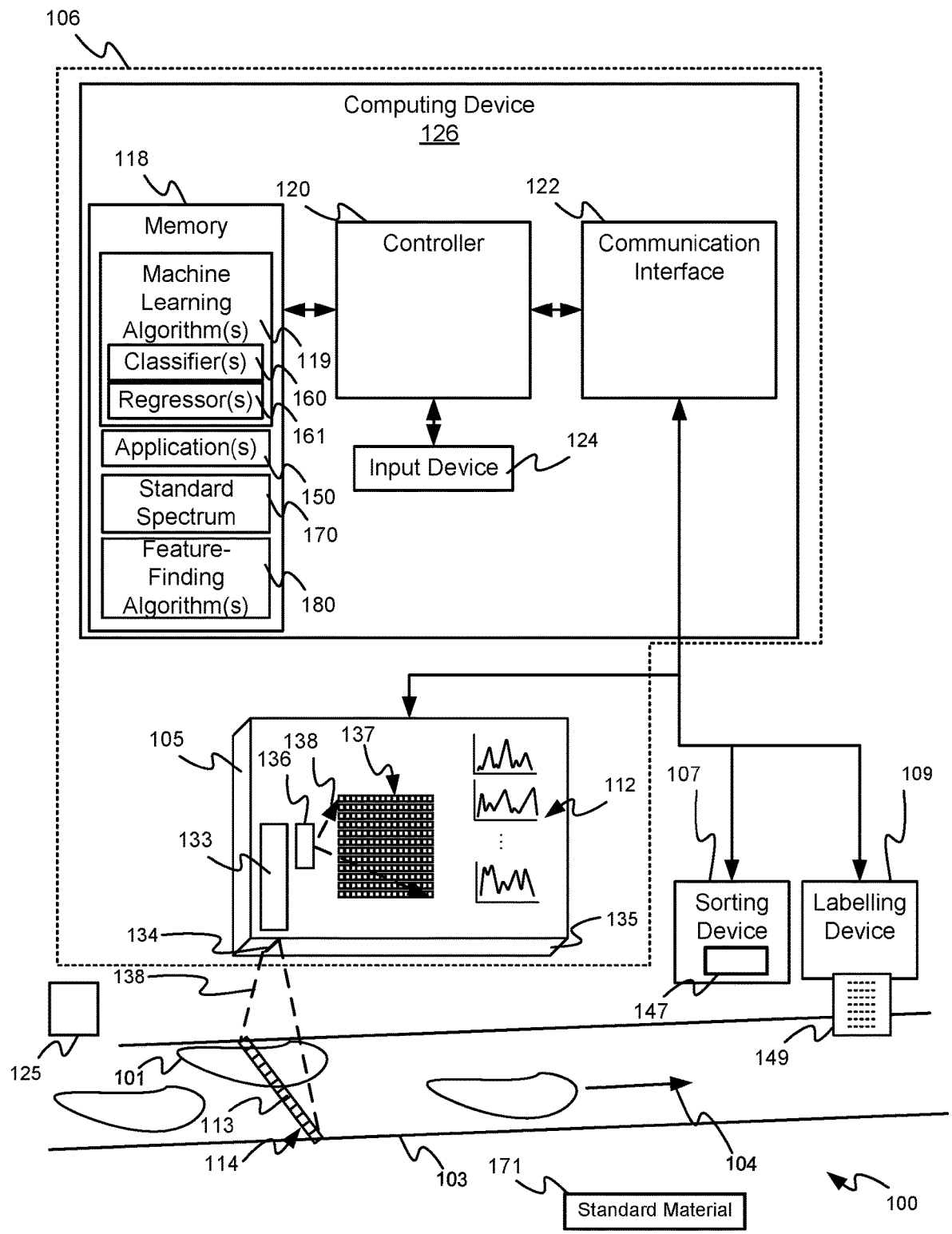
FIG. 1 depicts is a schematic view of a device and system for one or more of sorting and labeling food products using a line-scan dispersive spectrometer, in accordance with some examples.

A first aspect of the present specification provides a device for one or more of sorting and labeling food products, the device comprising: at least one line-scan dispersive spectrometer configured to acquire respective spectra of the food products for (e.g. each of) a plurality of segments of a line; a memory storing one or more machine learning algorithms trained to classify the respective spectra of the plurality of segments into categories indicative of one or more food parameters; and a controller in communication with the at least one line-scan dispersive spectrometer, the memory and one or more of a sorting device and a labeling device, the controller configured to: receive, from the at least one line-scan dispersive spectrometer, the respective spectra of the food products for (e.g. each of) the plurality of segments of the line; apply the one or more machine learning algorithms to the respective spectra to classify the plurality of segments according to at least one of the one or more food parameters; and control one or more of the sorting device and the labeling device according to classifying the plurality of segments to cause the food products to be one or more of sorted and labeled according to the at least one of the one or more food parameters. In some examples, the plurality of segments may be classified on a segment-by-segment basis. In other examples groups of the plurality of segments may be classified.

The first aspect of the present specification further provides a method for one or more of sorting and labeling food products, the method comprising: receiving, at a controller, from at least one line-scan dispersive spectrometer, respective spectra of food products for (e.g. each of) a plurality of segments of a line, at least one line-scan dispersive spectrometer configured to acquire respective spectra of the food products for (e.g. each of) the plurality of segments of the line; applying, at the controller, one or more machine learning algorithms to the respective spectra to classify the plurality of segments according to at least one of one or more food parameters; and controlling, at the controller, one or more of a sorting device and a labeling device according to classifying the plurality of segments to cause the food products to be one or more of sorted and labeled according to the at least one of the one or more food parameters.

A second aspect of the present specification provides a device for one or more of sorting and labeling food products, the device comprising: at least one line-scan dispersive spectrometer configured to acquire respective spectra of the food products for (e.g. each of) a plurality of segments of a line; a memory storing one or more machine learning algorithms trained to classify the respective spectra of the plurality of segments into categories indicative of one or more time distant events; and a controller in communication with the at least one line-scan dispersive spectrometer, the memory and one or more of a sorting device and a labeling device, the controller configured to: receive, from the at least one line-scan dispersive spectrometer, the respective spectra of the food products for (e.g. each of) the plurality of segments of the line; apply the one or more machine learning algorithms to the respective spectra to classify the plurality of segments according to at least one of the one or more time distant events; and control one or more of the sorting device and the labeling device according to classifying the plurality of segments to cause the food products to be one or more of sorted and labeled according to the at least one of the one or more time distant events. In some examples, the plurality of segments may be classified on a segment-by-segment basis. In other examples groups of the plurality of segments may be classified.

The second aspect of the present specification further provides a method for one or more of sorting and labeling food products, the method comprising: receiving, at a controller, from at least one line-scan dispersive spectrometer, respective spectra of food products for (e.g. each of) a plurality of segments of a line, at least one line-scan dispersive spectrometer configured to acquire respective spectra of the food products for (e.g. each of) the plurality of segments of the line; applying, at the controller, one or more machine learning algorithms to the respective spectra to classify the plurality of segments according to at least one of the one or more time distant events; and controlling, at the controller, one or more of a sorting device and a labeling device according to classifying the plurality of segments to cause the food products to be one or more of sorted and labeled according to the at least one of the one or more time distant events. In some examples, the plurality of segments may be classified on a segment-by-segment basis. In other examples groups of the plurality of segments may be classified.

The one or more time distant events may include one or more of: a geographic location of a source of the food products; a time period that the food products were produced; a production method of the food products; a farming method of the food products; a handling method of the food products; an expiry date of the food products; a transportation method of the food product from a source of the food products to one or more of a food product sorting facility and a food product labeling facility; a storage method of the food product prior to one or more of food product sorting and food product labeling; a pre-processing method of the food products which occurs prior to one or more of the food product sorting and the food product labeling; a handling method of the food products which occurs prior to one or more of the food product sorting and the food product labeling; a cleaning method of the food products which occurs prior to one or more of the food product sorting and the food product labeling; a flavour profile of the food products as detectable to a food product consumer after shipment of the food products from one or more of the food product sorting facility and the food product labeling facility; a quality profile of the food products as detectable to a food product consumer after shipment of the food products from one or more of the food product sorting facility and the food product labeling facility; a nutrition profile of the food products after shipment of the food products from one or more of the food product sorting facility and the food product labeling facility; and a phenotype expression of the food product after shipment of the food products from one or more of the food product sorting facility and the food product labeling facility.

A third aspect of the present specification provides a device for one or more of sorting and labeling food products, the device comprising: a first sensing device configured to acquire respective first sensed data of the food products for (e.g. each of) a plurality of first segments of a first line; a second sensing device configured to acquire respective second sensed data of the food products for (e.g. each of) a plurality of second segments of a second line, the first line and the second line each corresponding to a common line at the food products; a memory storing one or more machine learning algorithms trained to classify the plurality of first segments into categories indicative of one or more food parameters; and a controller in communication with the first sensing device, the second sensing device, the memory and a notification device, the controller configured to: receive, from (e.g. each of) the first sensing device and the second sensing device, the respective first sensed data and the respective second sensed data of the common sensed line; apply the one or more machine learning algorithms to the respective first sensed data to classify the plurality of first segments according to at least one of the one or more food parameters, the plurality of first segments classified on a segment-by-segment basis; classify the plurality of second segments according to at least one of the one or more food parameters based on classifications of corresponding first segments associated with the respective first sensed data; train the one or more machine learning algorithms to classify the plurality of second segments according to at least one of the one or more food parameters based on the respective second sensed data and classifications of the second segments as determined from the corresponding first segments associated with the respective first sensed data; and control one or more of a sorting device and a labeling device according to classifying one or more of the plurality of first segments and the plurality of second segments to cause the food products to be one or more of sorted and labeled according to the at least one of the one or more food parameters.

The first sensing device may comprise a line-scan dispersive spectrometer, and the respective first sensed data may comprise respective spectra of the food products for (e.g. each of) the plurality of first segments. The second sensing device may comprise a line-scan camera and the respective second sensed data may comprise line-scan images of the food products.

The first sensing device and the second sensing device may comprise different sensing device types, and the one or more machine learning algorithms may be trained to classify the respective first sensed data and the respective second sensed data based on different respective features of (e.g. each of) the respective first sensed data and the respective second sensed data.

The plurality of first segments and the plurality of second segments may have different segment resolutions and the controller may be further configured to determine correspondences between the plurality of first segments and the plurality of second segments prior to classifying the plurality of second segments associated with the respective second sensed data according to the at least one of the one or more food parameters based on the classifications of the corresponding first segments associated with the respective first sensed data.

The device may further comprise a third sensing device configured to acquire respective third sensed data of the food products for (e.g. each of) a plurality of third segments arranged along a third line corresponding to the common sensed line at the food products, and the controller may be further configured to: receive, from the third sensing device, the respective third sensed data of the common sensed line; apply the one or more machine learning algorithms to one or more of the respective first sensed data and the respective second sensed data to classify one or more of the plurality of first segments and the plurality of second segments according to at least one of the one or more food parameters, one or more of the plurality of first segments and the plurality of second segments classified on a segment-by-segment basis; classify the plurality of third segments associated with the respective third sensed data according to at least one of the one or more food parameters based on classifications of one or more of the corresponding first segments associated with the respective first sensed data and corresponding second segments associated with the respective second sensed data; train the one or more machine learning algorithms to classify the plurality of third segments according to at least one of the one or more food parameters based on the respective third sensed data and classifications of the plurality of third segments as determined from one or more of the corresponding first segments associated with the respective first sensed data and the corresponding second segments associated with the respective second sensed data; and control one or more of the sorting device and the labeling device according to classifying one or more of the plurality of first segments, the plurality of second segments and the plurality of third segments to cause the food products to be one or more of sorted and labeled according to the at least one of the one or more food parameters.

The third aspect of the present specification further provides a method for one or more of sorting and labeling food products, the method comprising: receiving, at a controller, from (e.g. each of) a first sensing device and a second sensing device, a respective first sensed data and a respective second sensed data of a common sensed line, the first sensing device configured to acquire respective the first sensed data of food products for (e.g. each of) a plurality of first segments of a first line, and the second sensing device configured to acquire the respective second sensed data of the food products for (e.g. each of) a plurality of second segments of a second line, the first line and the second line each corresponding to the common line at the food products; applying, using the controller, one or more machine learning algorithms to the respective first sensed data to classify the plurality of first segments according to at least one of one or more food parameters, the plurality of first segments classified on a segment-by-segment basis; classifying, using the controller, the plurality of second segments according to at least one of the one or more food parameters based on classifications of corresponding first segments associated with the respective first sensed data; training, using the controller, the one or more machine learning algorithms to classify the plurality of second segments according to at least one of the one or more food parameters based on the respective second sensed data and classifications of the second segments as determined from the corresponding first segments associated with the respective first sensed data; and controlling, using the controller, one or more of a sorting device and a labeling device according to classifying one or more of the plurality of first segments and the plurality of second segments to cause the food products to be one or more of sorted and labeled according to the at least one of the one or more food parameters.

The method may further comprise: receiving, at the controller, from a third sensing device, respective third sensed data of the common sensed line, the third sensing device configured to acquire the respective third sensed data of the food products for (e.g. each of) a plurality of third segments arranged along a third line corresponding to the common sensed line at the food products; applying, using the controller, the one or more machine learning algorithms to one or more of the respective first sensed data and the respective second sensed data to classify one or more of the plurality of first segments and the plurality of second segments according to at least one of the one or more food parameters, one or more of the plurality of first segments and the plurality of second segments classified on a segment-by-segment basis; classifying, using the controller, the plurality of third segments associated with the respective third sensed data according to at least one of the one or more food parameters based on classifications of one or more of the corresponding first segments associated with the respective first sensed data and corresponding second segments associated with the respective second sensed data; training, using the controller, the one or more machine learning algorithms to classify the plurality of third segments according to at least one of the one or more food parameters based on the respective third sensed data and classifications of the plurality of third segments as determined from one or more of the corresponding first segments associated with the respective first sensed data and the corresponding second segments associated with the respective second sensed data; and controlling, using the controller, one or more of the sorting device and the labeling device according to classifying one or more of the plurality of first segments, the plurality of second segments and the plurality of third segments to cause the food products to be one or more of sorted and labeled according to the at least one of the one or more food parameters.

A fourth aspect of the present specification provides a device for one or more of sorting and labeling food products, the device comprising: a sensing device configured to acquire respective sensed data of the food products for (e.g. each of) a plurality of segments arranged along a line; a communication interface; a memory storing one or more machine learning algorithms trained to classify the plurality of segments into categories into categories indicative of one or more food parameters; and a controller in communication with the sensing device, the communication interface, the memory and one or more of a sorting device and a labeling device, the controller configured to: receive, from the sensing device, the respective sensed data of the food products for (e.g. each of) the plurality of segments of the line; apply the one or more machine learning algorithms to the respective sensed data to classify the plurality of segments according to at least one of the one or more food parameters; identify, from the respective sensed data, an unknown feature not recognized by the one or more machine learning algorithms; control one or more of the sorting device and the labeling device to cause one or more of sorting and labeling of a respective food product at which the unknown feature was detected; receive, via one more of the communication interface and an input device, feedback to classify the unknown feature as a learned feature; and update the one or more machine learning algorithms to classify the plurality of segments according to the learned feature such that respective segments associated with further sensed data of further food products are classified according to one or more of the learned feature and at least one of the one or more food parameters. In some examples, the plurality of segments may be classified on a segment-by-segment basis. In other examples groups of the plurality of segments may be classified.

The sensing device may comprise a line-scan dispersive spectrometer, the respective sensed data may comprise respective spectra of the food products for (e.g. each of) the plurality of segments, and the controller may be further configured to identify the unknown feature by: may comprise detecting an unknown spectral feature in the respective spectra.

The feedback may be received, via the communication interface, from a remote computing device and/or the feedback may be received locally, via the input device. Hence, the feedback may be received via one or more of the communication interface and the input device.

The fourth aspect of the present specification may further provide a method for one or more of sorting and labeling food products, the method comprising: receiving, at a controller, from a sensing device, respective sensed data of food products for (e.g. each of) a plurality of segments of a line, the sensing device configured to acquire the respective sensed data of the food products for (e.g. each of) the plurality of segments arranged along the line; applying, using the controller, one or more machine learning algorithms to the respective sensed data to classify the plurality of segments according to at least one of the one or more food parameters; identifying, using the controller, from the respective sensed data, an unknown feature not recognized by the one or more machine learning algorithms; controlling, using the controller, one or more of a sorting device and a labeling device to cause one or more of sorting and labeling of a respective food product at which the unknown feature was detected; receiving, at the controller, via one more of a communication interface and an input device, feedback to classify the unknown feature as a learned feature; and updating, using the controller, the one or more machine learning algorithms to classify the plurality of segments according to the learned feature such that respective segments associated with further sensed data of further food products are classified according to one or more of the learned feature and at least one of the one or more food parameters. In some examples, the plurality of segments may be classified on a segment-by-segment basis. In other examples groups of the plurality of segments may be classified.

The feedback may comprise one or more of: expert feedback; one or more of a machine learning classifier and a machine learning regressor of the learned feature; a specific identification of a food impurity; a chemical identification of a food impurity; a chemical composition of a food product; a pH of a food product; an amount of sugar in a food product; a water holding capacity of a food product; a physical measurement of a food product; a fat content of a food product; a protein content of a food product; a water content of a food product; a lean content of a food product; a tenderness of a food product; a juiciness of a food product; a color of a food product; an integrity measurement of a food product; a flavor of a food product; a quality of a food product; and marbling of a food product.

A fifth aspect of the present specification provides a device for one or more of sorting and labeling food products, the device comprising: at least one line-scan dispersive spectrometer configured to acquire respective spectra of the food products for (e.g. each of) a plurality of segments of a line; a communication interface; a memory storing one or more machine learning algorithms; and a controller in communication with the at least one line-scan dispersive spectrometer, the communication interface and the memory, the controller configured to: receive, from the at least one line-scan dispersive spectrometer, the respective spectra of the food products for (e.g. each of) the plurality of segments of the line; apply a clustering algorithm to group one or more of the respective spectra and spectral features of the respective spectra into a plurality of groups; receive, via the communication interface, feedback to classify the plurality of groups according to one or more food parameters; update the one or more machine learning algorithms to classify the plurality of segments according to the feedback such that respective segments associated with further respective spectra of further food products are classified according to at least one of the one or more food parameters.

The feedback may be received, via the communication interface, from a remote computing device and/or the feedback may be received locally, via the input device. Hence, the feedback may be received via one or more of the communication interface and the input device.

The feedback may comprise one or more of: one or more of a machine learning classifier and a machine learning regressor of at least one of the one or more food parameters; and expert feedback.

The controller may be further configured to control one or more of a sorting device and a labeling device to one or more of sort and label the food products according to the plurality of groups such that the food products are examined by one or more of a measurement device and an expert to provide the feedback.

The fifth aspect of the present specification further provides a method for one or more of sorting and labeling food products, the method comprising: receiving, at a controller, from the at least one line-scan dispersive spectrometer, respective spectra of food products for (e.g. each of) a plurality of segments of a line, the at least one line-scan dispersive spectrometer configured to acquire the respective spectra of the food products for (e.g. each of) the plurality of segments of the line; applying, using the controller, a clustering algorithm to group one or more of the respective spectra and spectral features of the respective spectra into a plurality of groups; receiving, at the controller, via a communication interface, feedback to classify the plurality of groups according to one or more food parameters; updating, using the controller, one or more machine learning algorithms to classify the plurality of segments according to the feedback such that respective segments associated with further respective spectra of further food products are classified according to at least one of the one or more food parameters.

The method may further comprise controlling, using the controller, one or more of a sorting device and a labeling device to one or more of sort and label the food products according to the plurality of groups such that the food products are examined by one or more of a measurement device and an expert to provide the feedback.

A sixth aspect of the present specification provides a computing device comprising: a communication interface configured to communicate with a plurality of sensing devices at a plurality of locations, (e.g. each of) the plurality of sensing devices configured to acquire respective sensed data of similar food products for a respective plurality of segments arranged along a respective line; a memory storing one or more machine learning algorithms trained to classify the respective sensed data of the respective plurality of segments into categories indicative of one or more food parameters; and a controller in communication with the communication interface and the memory, the controller configured to: receive, via the communication interface, from the plurality of sensing devices, the respective sensed data of the similar food products for the respective plurality of segments; receive, via the communication interface, feedback to classify the respective sensed data according to one or more of food parameters; further train the one or more machine learning algorithms to classify the respective plurality of segments according to the feedback and the respective sensed data to update at least one of: one or more respective machine learning classifiers and respective machine learning regressors corresponding to at least one of the one or more food parameters; and the one or more machine learning algorithms; and provide, via the communication interface, to one or more of the plurality of sensing devices, the one or more respective machine learning classifiers and the respective machine learning regressors to update respective machine learning algorithms at the one or more of the plurality of sensing devices such that respective segments of further respective sensed data of further food products are classified at the one or more of the plurality of sensing devices according to the at least one of the one or more food parameters.

The sixth aspect of the present specification further provides a method comprising: receiving, at a controller, via a communication interface, from a plurality of sensing devices, respective sensed data of similar food products for a respective plurality of segments arranged along a respective line, the plurality of sensing devices at a plurality of locations, (e.g. each of) the plurality of sensing devices configured to acquire the respective sensed data of the similar food products for the respective plurality of segments arranged along the respective line, the controller in communication with a memory storing one or more machine learning algorithms trained to classify the respective sensed data of the respective plurality of segments into categories indicative of one or more food parameters; receiving, at the controller, via the communication interface, feedback to classify the respective sensed data according to one or more of food parameters; further training, using the controller, the one or more machine learning algorithms to classify the respective plurality of segments according to the feedback and the respective sensed data to update at least one of: one or more respective machine learning classifiers and respective machine learning regressors corresponding to at least one of the one or more food parameters; and the one or more machine learning algorithms; and providing, using the controller, via the communication interface, to one or more of the plurality of sensing devices, the one or more respective machine learning classifiers and the respective machine learning regressors to update respective machine learning algorithms at the one or more of the plurality of sensing devices such that respective segments of further respective sensed data of further food products are classified at the one or more of the plurality of sensing devices according to the at least one of the one or more food parameters.

Attention is directed to FIG. 1, which depicts a system 100 for one or more of sorting and labeling food products 101, for example in a food product manufacturing environment and/or food product processing environment and/or food packaging environment, and the like. In particular, the system 100 may be located at one or more of a food sorting facility, a food labeling facility, a food processing facility, and the like.

As depicted the food products 101 are being conveyed along a food product path such as a conveyor 103 and the like, for example in a food product path direction 104 (e.g. from left to right with respect to FIG. 1), the food products 101 being optically analyzed while being conveyed on the conveyor 103 for example by at least one line-scan dispersive spectrometer 105 that may be a component of a device 106 for one or more of sorting and labeling the food products 101.

While the food products 101 are depicted as slabs (e.g. meat), the food products 101 may include any type of food product such as meat, poultry seafood, fruits, vegetables, processed foods, ground products (e.g. such as ground meat, ground poultry, ground seafood, and the like), liquids (e.g. soups, and the like), and the like. While the conveyor 103 is depicted as being configured to convey the food products 101 in a horizontal direction, in other examples, the conveyor 103 may convey the food products 101 in a non-horizontal direction, for example at an angle upwards or downwards. Indeed, when the food products 101 are conveyed at an angle downwards, the conveyor 103 and/or a food product path may comprise a chute, and the like, along which the food products slide. Alternatively, when the food products 101 include liquids, the conveyor 103 may include piping. Alternatively, the system 100 may include the food products 101 being conveyed in a waterfall food product path such that the food products 101 fall, for example from a first conveyor to a second conveyor, the food products 101 being optically analyzed while falling (e.g. the food product path direction 104 may alternatively be in a downward direction). Alternatively, the conveyor 103 may include a gap (e.g. the conveyor 103 may include two conveyors with a gap therebetween) and the food products 101 may be optically analyzed from below, through the gap, and/or the food products 101 may be optically analyzed from both sides of the gap (e.g. from above and below the gap). Alternatively, the conveyor 103 may include one or more conveyors arranged in a "Z" configuration which flips the food products 101 (e.g. the food product path direction 104 may alternatively change directions along the conveyor 103), and the food products may be optically analyzed on opposing sides, for example by at least two line-scan dispersive spectrometers (and/or other sensing devices, as described below). Hence, while present examples are described with respect to the conveyor 103, the conveyor 103 may interchangeably be referred to herein as the food product path regardless of whether the conveyor 103 includes a waterfall, piping, and the like. Regardless, in present examples, the food products 101 are generally conveyed in the food product path direction 104 and optically analyzed, for example by the line-scan dispersive spectrometer 105 and/or device 106, and one or more of sorted and labeled along the food product path, for example by one or more of a sorting device 107 and a labeling device 109, described in more detail below.

In particular, as depicted, the device 106 comprises: the at least one line-scan dispersive spectrometer 105 configured to acquire respective spectra 112 of the food products 101 for (e.g. each of) a plurality of segments 113 of a line 114; a memory 118 storing one or more machine learning algorithms 119 trained to classify the respective spectra 112 of the plurality of segments 113 into categories indicative of one or more food parameters; and a controller 120 in communication with the at least one line-scan dispersive spectrometer 105, the memory 118 and one or more of the sorting device 107 and the labeling device 109. As depicted, the controller 120 is in communication with one or more of the sorting device 107 and the labeling device 109 via a communication interface 122. As depicted, the device 106 further comprises an input device 124, which may include, but is not limited to any suitable combination of, a keyboard, a touchscreen, a pointing device, and the like; in some examples, the input device 124 is optional.

As depicted, the system 100 and/or the device 106 further comprises a lamp 125 for illuminating the food products 101 at the line 114, for example according to a known spectrum and/or given spectrum.

Furthermore, the line 114 need not be strictly perpendicular to the food product path direction 104 and may be at any suitable angle thereto. However, the line 114 may extend from side-to-side across the conveyor 103 (e.g. a food product path), though the orientation and/or dimensions of the line 114 is generally defined by optics of the line-scan dispersive spectrometer 105 and/or the relative position of the line-scan dispersive spectrometer 105 with respect to the conveyor 103.

Furthermore, as depicted, the memory 118, the controller 120 and the communication interface 122 are located at a computing device 126. In some examples, the computing device 126 may comprise a computing device of the line-scan dispersive spectrometer 105, while in other examples, the computing device 126 and the line-scan dispersive spectrometer 105 may be different from one another and/or in communication via one or more wireless or wired communication links. Indeed, communication links between components of the system 100 are depicted in FIG. 1, and throughout the present specification, as double-ended arrows between respective components. Hence, the components of the device 106 may not all be co-located and/or components of the device 106 may be distributed over more than one location; for example, the computing device 126 may comprise one or more cloud-computing devices in communication with the line-scan dispersive spectrometer 105 and one or more of the sorting device 107 and the labeling device 109 via one or more communication networks and/or communication links via the communication interface 122. As such, the device 106 is indicated using dashed lines that include the computing device 126 and the line-scan dispersive spectrometer 105 to indicate that the components of the device 106 may be distributed and/or not co-located.

In yet further examples, one or more of the sorting device 107 and the labeling device 109 may be components of the device 106.

In general, the line-scan dispersive spectrometer 105 is arranged relative to the conveyor 103 such that (e.g. each of) the plurality of segments 113 arranged along the line 114 corresponds to regions at the conveyor 103, for example, as depicted, from side-to-side across the conveyor 103 and/or perpendicular to a food product path. Furthermore, a calibration process may be used to determine whether the plurality of segments 113 is arranged perpendicular to a food product path and the line-scan dispersive spectrometer 105 may be adjusted accordingly, and the like. In some examples, at least a portion of the conveyor 103 may be a component of the device 106.

Indeed, while the system 100 and/or the device 106 is depicted as including only one line-scan dispersive spectrometer 105, the system 100 and/or the device 106 may comprise more than one line-scan dispersive spectrometer, for example two line-scan dispersive spectrometers arranged side by side to optically analyze respective portions of the segments 113 and/or the line 114 across the conveyor 103, such that the line-scan dispersive spectrometer 105 images and/or optically analyzes segments 113 of a first half of the line 114, and a second line-scan dispersive spectrometer images and/or optically analyzes segments 113 of a second half of the line 114, for example to obtain a particular segment resolution along the line 114. Indeed, the system 100 may include any suitable number of line-scan dispersive spectrometers arranged in any suitable manner. For example, two (or more) line-scan dispersive spectrometers may be arranged side by side such that one optically analyzes a portion of the segments 113 (e.g. at a right side of the conveyor 103) and the other optically analyzes another portion of the segments 113 (e.g. at a left side of the conveyor 103). Alternatively, two (or more) line-scan dispersive spectrometers may be arranged along the conveyor 103 (e.g. one after another), each arranged to optically analyze the segments 113 in different spectral domains. Alternatively, two (or more) line-scan dispersive spectrometers may arranged along the conveyor 103 (e.g. one after another), each arranged to optically analyze the food products 101 along different sets of segments (e.g. a first line-scan dispersive spectrometers configured to optically analyze the food products 101 the segments 113 and a second line-scan dispersive spectrometers configured to optically analyze the food products 101 further down the conveyor 103 at segments of the food products 101 that correspond to the segments 113), with the spectra from each coordinated based on a speed of the conveyor 103, and the like.

In yet further examples the system 100 and/or the device 106 may comprise a plurality of line-scan spectrometers arranged along the conveyor 103 and/or the food product path. For example, the device 106 may comprise the line-scan dispersive spectrometer 105 and at least a second line-scan dispersive spectrometer located further down the conveyor 103 and/or the food product path. For example, the conveyor 103 and/or the food product path may be in a "Z" configuration which causes the food products 101 to flip and/or be turned over to expose a side opposite a side depicted in FIG. 1; in these examples, the line-scan dispersive spectrometer 105 may image and/or optically analyze a first side of the food products 101, and the second line-scan dispersive spectrometer may image and/or optically analyze a second side of the food products 101 the second side being opposite the first side.

Hence the at least one line-scan dispersive spectrometer 105 is interchangeably referred to herein as the line-scan dispersive spectrometer 105.

The line-scan dispersive spectrometer 105 may further include an enclosure compatible with a food processing environment, and in which other components of the line-scan dispersive spectrometer 105 are enclosed. Indeed, the line-scan dispersive spectrometer 105 and/or the system 100 may include any other suitable components; for example, the line-scan dispersive spectrometer 105 and/or the system 100 generally includes one or more lights as described below.

Indeed, FIG. 1 further schematically depicts operation and components of the line-scan dispersive spectrometer 105. In particular, the line-scan dispersive spectrometer 105 includes any suitable optics 133 (e.g. any suitable combination of mirrors, lenses, optical filters, beam-splitters, prisms and the like) which conveys light from the line 114 through a slit 134, and the like, in a food-product facing side 135 (e.g. a side of the enclosure) of the line-scan dispersive spectrometer 105 to a transmission grating and/or a holographic transmission grating 136, and the like, which disperses the light of (e.g. each of) the segments 113 to a plurality of light sensors 137 disposed in an array and positioned to receive the dispersed light of (e.g. each of) the segments 113 from grating 136. Indeed, while the line-scan dispersive spectrometer 105 is described as including the transmission holographic transmission grating 136, the line-scan dispersive spectrometer 105 may include any suitable device with similar functionality, including, but not limited to a transmission grating, a grism (e.g. a grating sandwiched between prisms), a prism, a spatially changing filter (e.g. which only lets certain bands of light onto specific detector pixels), and/or any other suitable light dispersing device including, but not limited to, active devices such as MEMS (micro-electromechanical system) devices, and the like.

The sensors 137 of the array are arranged in rows and/or columns; for example, as depicted, the sensors 137 are arranged in horizontal rows in FIG. 1 but it is understood that the sensors 137 may also be arranged in columns, though rows of sensors 137 will be referred to hereafter. As depicted, light 138 from each segment 113 is dispersed according to wavelength across a respective row of sensors 137, according to the optical properties of the grating 136, such that each sensor 137 in each row of sensors 137 images and/or optically analyzes a particular wavelength of the light 138 and/or particular group of wavelengths of the light 138. For example, light of a particular wavelength and/or a particular group of wavelengths, as dispersed by the grating 136, will interact with a given sensor 137, which will responsively generate a signal indicative of the intensity of the particular wavelength and/or a particular group of wavelengths. While not depicted, the line-scan dispersive spectrometer 105 generally further comprise suitable optics for focusing light from the grating 136 onto the sensors 137; however, the grating 136 may also be configured to at least partially focus the light onto the sensors 137.

The collective output from a row (or column) of sensors 137 in the array for a particular segment 113 of the line 114 corresponds to a respective spectra 112 for the particular segment 113. The resulting spectra 112 may be referred to interchangeably as spectroscopic images and/or spectroscopic line-scan images. The spectra 112 for the segments 113 of the line 114 may be conveyed to the controller 120 for analysis as described in further detail below.

By selecting the grating 136 with particular optical properties, and by selecting positioning of the sensors 137 in the array, the line-scan dispersive spectrometer 105 may be configured to generate the spectra 112 for given ranges of wavelengths. Similarly, by selecting the optics 133, and/or a position of the line-scan dispersive spectrometer 105 with respect to the conveyor 103, a resolution of the segments 113 of the line 114 may be selected.

Furthermore, as a given food product 101 is conveyed across the line 114, the line-scan dispersive spectrometer 105 may collect the spectra 112 at a given rate, which may be coordinated with a speed of the conveyor 103, such that the spectra 112 may be collected and analyzed across the given food product 101. Hence, by selecting a rate of movement of the conveyor 103 and/or by selecting an acquisition rate of the spectra 112, the resolution of the segments 113 in the food product path direction 104 may be selected.

Indeed, line-scan dispersive spectrometer 105 may collect the spectra 112 at a given rate, on a line-by-line basis, such that spectra 112 for successive lines 114 of the segments 113 are collected at the given rate. By controlling the speed of the conveyor 103, relative to the given rate of spectra collection, the resolution of data collection for the food products 101 may be controlled. For example, the speed of the conveyor 103, relative to the given rate of spectra collection may be controlled such that spectra 112 for successive lines 114 of the segments 113 are collected for overlapping regions of the food products and/or adjacent regions of the food products 101, and/or separated regions of the food products 101.

For example, the line-scan dispersive spectrometer 105 may be arranged relative to the conveyor 103 such that (e.g. each of) the plurality of segments 113 arranged along the line 114 corresponds to between about 0.5 mm and about 5 mm along the conveyor 103.

Hence, in some examples, spectra 112 for regions of a food product 101 may be collected, according to a segment resolution, and analyzed by the controller 120 to determine food parameters of the various regions of the food product 101 that correspond to segments 113. Furthermore, as described below aggregate food parameters of the food product 101 may be determined from a collection of spectra 112 of the regions of the food product 101.

In further examples, the line-scan dispersive spectrometer 105 may have a segment resolution and/or food product imaging resolution of at least 128 segments across the line 114, which is generally indicative of a number of rows of the sensors 137 in the array of sensors 137 (e.g. 128 segments across the line 114 may correspond to 128 rows of sensors 137 in the array of sensors 137). However, the line-scan dispersive spectrometer 105 may have a higher segment resolution and/or food product imaging resolution; for example, the line-scan dispersive spectrometer 105 may have a segment resolution and/or food product imaging resolution of at least 512 segments across the line 114.

The resolution of the spectra 112 is generally dependent on a number of sensors 137 in each row. In some examples, the line-scan dispersive spectrometer 105 the includes sensors 137 for detecting wavelengths of (e.g. each of) the plurality of segments 113, and the line-scan dispersive spectrometer 105 has a spectral resolution of one or more of: at least 128 wavelengths (e.g. 128 sensors 137 in a row of sensors 137 in the array); and less than or equal to about 10 nm between adjacent sensors 137. In the examples, where the spectral resolution is about 10 nm between adjacent sensors 137, the sensors 137 may sense wavelengths of light in about 10 nm intervals, which may be determined by the positioning of the sensors 137 relative to the spread of the wavelengths of light by the grating 136. In particular examples, the resolution of the spectra 112 may be 512 and/or the line-scan dispersive spectrometer 105 may include 512 sensors 137 in each row. In further particular examples, the resolution of the spectra 112 may be 640 and/or the line-scan dispersive spectrometer 105 may include 640 sensors 137 in each row In some examples, the line-scan dispersive spectrometer 105 may be further configured to acquire the respective spectra 112 in a wavelength range of one or more of (e.g. with the spectral resolution depend on a number of sensors 137 in a row): about 250 nm to about 900 nm; about 350 nm to about 1050 nm; about 700 nm to about 2200 nm; about 900 nm to 1700 nm; about 900 nm to about 2500 nm; about 800 nm to about 1700 nm; about 350 nm to about 800 nm; about 350 nm to about 1700 nm; and about 250 nm to about 2700 nm. Indeed, the line-scan dispersive spectrometer 105 may be configured to acquire the respective spectra 112 in a plurality of wavelength ranges, which all fall in range of between about 250 nm to about 2700 nm. Again, the wavelength range(s) of the line-scan dispersive spectrometer 105 may be determined by the positioning of the sensors 137 relative to the spread of the wavelengths of light by the grating 136. Indeed, the grating 136 may be selected to disperse given wavelength ranges across the sensors 137 and/or the line-scan dispersive spectrometer 105 may be provided with a plurality of slits 134 and/or gratings 136 and/or a plurality of arrays of sensors 137 for generating spectra 112 for different wavelength ranges, with the optics 133 adjusted accordingly to convey the light 138 thereto. In yet further examples, the line-scan dispersive spectrometer 105 may be provided with a plurality of gratings 136 for optically dispersing different wavelength ranges, and which may be mounted in a manner that enables swapping of the plurality of gratings 136 with respect to the sensors 137, to optically analyzed the different wavelength ranges.

The respective spectra 112 of the food products 101 may be transmitted to the controller 120 and/or the computing device 126 (and/or the transmission may occur within the device 106) for analysis to determine one or more food parameters of the food products 101 in the segments 113 of the line 114. For example, the one or more food parameters may include parameters indicative of one or more of food quality, food impurities, food contaminants and the like.

For example, food impurities and/or food contaminants such as plastic, safety glove clippings, bone fragments and the like have signature spectra in a range of about 800 nm to 2000 nm and/or in a range of 800 nm to 2700 nm. Similarly, meat products, protein, fat, lean, bone, cartilage, etc., have signature spectra in a range of about 800 nm to 2000 nm and/or in a range of 800 nm to 2700 nm. Similarly, fruits and vegetables, and/or other types of food products, have signature spectra in a range of about 800 nm to 2000 nm and/or in a range of 800 nm to 2700 nm. Hence, as described herein, by analyzing spectra 112 of segments 113 of the line 114 using the one or more machine learning algorithms 119, different types of impurities and/or contaminants and/or different types of food product types may be determined, and/or a quality of the food product 101 may be determined, for example, on a segment-by-segment basis from the line 114; and/or different types of impurities and/or contaminants and/or different types of food product types may be determined, and/or a quality of the food product 101 may be determined for groups of the segments 113; and/or different types of impurities and/or contaminants and/or different types of food product types may be determined, and/or a quality of the food product 101 may be determined for adjacent segments 113; and/or different types of impurities and/or contaminants and/or different types of food product types may be determined, and/or a quality of the food product 101 may be determined for any other suitable groupings of the segments 113.

Indeed, the one or more machine learning algorithms 119 may be trained to determine, from the spectra 112, one or more of: chemical composition of a food product 101, a pH of a food product 101, a water holding capacity of a food product 101, a physical measurement of a food product 101, a fat content of a food product 101, a protein content of a food product 101, a water content of a food product 101, a lean content of a food product 101, a tenderness of a food product 101, a juiciness of a food product 101, a color of a food product 101, an integrity measurement of a food product 101, a flavor of a food product 101, marbling of a food product 101, an amount of a specific nutrient (e.g. vitamins, minerals, and the like) in a food product 101, and the like.

However, as will also be described hereafter, the one or more machine learning algorithms 119 may also be trained to determine time-distant events associated with the food products 101 to determine, for example, one or more of provenance, handling, processing, and the like, of the food products 101, and/or a prediction of one or more of an expiry date, a best-before date, a use-by date, a flavor profile, a quality profile, a nutrition profile, a phenotype expression, and the like, of the food products 101 after shipping from the food processing facility (e.g. and/or the facility where the line-scan dispersive spectrometer 105 is located).

Indeed, the spectra 112 may generally provide detailed information about chemical profiles and/or chemical composition of the food products, for example on a segment-by-segment basis, for groups of segments 113, and the like, which may provide more information than a simple camera image. Hence, using the one or more machine learning algorithms 119 to analyze the spectra 112 may provide more information about the food products 101 than using machine learning algorithms to analyze simple camera images of the food products 101.

The sorting device 107 and/or the labeling device 109 may be controlled by the device 106 and/or the computing device 126 to sort and/or label the food products 101 according to at least one of the food parameters determined using the one or more machine learning algorithms 119.

As depicted, the sorting device 107 may comprise a notification device 147, such as one or more of a display screen, lights, a speaker, and the like, which is controlled to provide an indication of at least one of the food parameters, for example to cause and/or instruct a food handler to sort a given food product 101 accordingly. However, the sorting device 107 may alternatively comprise a mechanical arm, a retractable portion, an air jet and the like, for removing and/or diverting a given food product 101 from the conveyor 103 (e.g. to another conveyor and/or another food product path) to sort the given food product 101 according to at least one of the food parameters. Regardless, the sorting device 107 causes a given food product 101 to be sorted on the basis of at least one of the food parameters as determined for the given food product 101 by the one or more machine learning algorithms 119.

The labeling device 109 may be configured to generate labels 149 that provide an indication of at least one of the food parameters (e.g. graphically and/or textually) which may be used to label containers, and the like, into which a given food product 101 is packaged. However, generation of labels as described herein may include, but is not limited to, printed labels, laser-printer labels (e.g. as laser-printed on the food products 101) electronic labels (e.g. as stored in a database), and the like.

The sorting device 107 and the labeling device 109 may be co-located, or the sorting device 107 and the labeling device 109 may be at different locations along the conveyor 103. Furthermore, the system 100 may comprise one of the sorting device 107 or the labeling device 109, but not the other of the sorting device 107 and the labeling device 109.

The components of the computing device 126 are next described in detail.

The computing device 126, may comprise any suitable computing device, including but not limited to, a graphics processing device, a graphics processing engine, a video processing device, a personal computer (PC), a server, a cloud-based computing device, and the like, and generally comprises the memory 118 storing the one or more machine learning algorithms 119, the controller 120; and the communication interface 122 (interchangeably referred to hereafter as the interface 122). While the memory 118 is depicted as internal to the computing device 126, the memory 118 may be external to the computing device 126 and the controller 120 may have access to the memory 118 via the interface 122.

As depicted, the memory 118 further stores one or more applications 150 which may be for implementing the one or more machine learning algorithms 119, training the one or more machine learning algorithms, and/or operating the system 100 and/or the device 106 and/or the computing device 126 and/or the device 106 in different modes. For simplicity, one or more applications 150 will be interchangeably referred to hereafter as the application 150.

The interface 122 comprises any suitable wired or wireless communication interface configured to communicate with the line-scan dispersive spectrometer 105, the sorting device 107 and/or the labeling device 109, and/or with any suitable cloud-based computing devices. The interface 122 may communicate in a wired and/or wireless manner as desired including, but not limited to, using cables, WiFi communication links, Bluetooth™ communication links, personal area networks, local area networks, and the like.

The controller 120 may comprise a processor and/or a plurality of processors, including but not limited to one or more central processors (CPUs) and/or one or more graphics processing units (GPUs) and/or neural processing units (NPUs) and/or one or more processing units; either way, the controller 120 comprises a hardware component and/or a hardware processor. Indeed, in some implementations, the controller 120 may comprise an ASIC (application-specific integrated circuit) and/or an FPGA (field-programmable gate array) specifically configured for one or more of sorting and labeling food products. Hence, the computing device 126 may preferably not be a generic computing device, but a device specifically configured to implement specific functionality for one or more of sorting and labeling food products. For example, the computing device 126 and/or the controller 120 may specifically comprise a computer executable engine configured to implement functionality for one or more of sorting and labeling food products.

The memory 118 may comprise a non-volatile storage unit (e.g. Erasable Electronic Programmable Read Only Memory ("EEPROM"), Flash Memory) and a volatile storage unit (e.g. random-access memory ("RAM")). Programming instructions that implement the functional teachings of the computing device 126 as described herein are typically maintained, persistently, in the memory 118 and used by the controller 120 which makes appropriate utilization of volatile storage during the execution of such programming instructions. Those skilled in the art recognize that the memory 118 is an example of computer readable media that may store programming instructions executable on the controller 120. Furthermore, the memory 118 is also an example of a memory unit and/or memory module and/or a non-volatile memory.

In particular, the memory 118 stores the application 150 that, when processed by the controller 120, enables the controller 120 and/or the computing device 126 and/or the device 106 to operate in at least one mode. In particular, in a first mode, which is described in further detail below with respect to FIG. 2, the application 150, when processed by the controller 120, enables the controller 120 and/or the computing device 126 and/or the device 106 to: receive, from the at least one line-scan dispersive spectrometer 105, the respective spectra 112 of the food products for (e.g. each of) the plurality of segments 113 of the line 114; apply the one or more machine learning algorithms 119 to the respective spectra 112 to classify the plurality of segments 113 according to at least one of one or more food parameters; and control one or more of the sorting device 107 and the labeling device 109 according to classifying the plurality of segments 113 to cause the food products 101 to be one or more of sorted and labeled according to the at least one of the one or more food parameters. In some examples, the plurality of segments 113 may be classified on a segment-by-segment basis, and in other examples groups of the plurality of segments 113 may be classified.

The one or more machine learning algorithms 119 may include, but are not limited to: a generalized linear regression algorithm; one or more deep learning algorithms; one or more neural networks; a random forest algorithm; a support vector machine algorithm; a gradient boosting regression algorithm; a decision tree algorithm; a generalized additive model; neural network algorithms; evolutionary programming algorithms; Bayesian inference algorithms, reinforcement learning algorithms, and the like. However, any suitable machine learning algorithms are within the scope of present examples.

In particular, the one or more machine learning algorithms 119 include respective classifiers 160 and/or regressors 161 indicative of the one or more food parameters, the respective classifiers 160 and/or regressors 161 generated from line-scan dispersive spectrometer spectra corresponding to the one or more food parameters. For example, as depicted, the one or more machine learning algorithms 119 have been trained from previously received spectra 112 and/or feedback classifying the previously received spectra from the line-scan dispersive spectrometer 105 (and/or another line-scan dispersive spectrometer), to classify the spectra 112 according to at least one of the one or more food parameters. The classifiers 160 and/or regressors 161 hence each generally represent a given food parameter that the one or more machine learning algorithms 119 have been trained to detect based on line-scan dispersive spectrometer spectra. Hence, for example, the one or more machine learning algorithms 119 may receive the spectra 112 for (e.g. each of) the segments 113, and compare the spectra 112 with the classifiers 160 and/or regressors 161, and/or process the spectra 112 with the classifiers 160 and/or regressors 161, to classify the spectra 112, and hence classify the segments 113, for example on a segment-by-segment basis (e.g. each segment 113 is classified using an associated spectra 112) and/or in any other suitable manner (e.g. groups of segments 113 and/or adjacent segments 113 may be classified using associated spectra 112, and the like). As such a collection of spectra 112 for a given food product 101 may be used to classify segments 113 for the given food product 101 to determine how the given food product 101 is to be sorted and/or labeled. In general, the classifiers 160 may be used to classify the segments 113 according to discrete values, and the regressors 161 may be used to classify the segments 113 according to continuous values.

As depicted, the memory 118 further stores at least one standard spectrum 170 which may be used in a calibration of the system 100. In particular, the standard spectrum 170 may comprise a line-scan dispersive spectrometer spectrum of piece of a material 171 such as Teflon™, and the like, with known properties, and which has been preconfigured at the memory 118. For example, the standard spectrum 170 may have been obtained using a well-calibrated line-scan dispersive spectrometer (e.g. low noise and/or with all associated sensors in good working order) and the material 171 (and/or another piece of the material 171), such that the standard spectrum 170 represents the known properties of the material 171. Prior to operation of the system 100 to one or more of sort and label the food products 101 (and/or periodically), the piece of the material 171 corresponding to the standard spectrum 170 may be scanned using the line-scan dispersive spectrometer 105, to obtain spectra thereof, for example for (e.g. each of) the segments 113 (and hence for (e.g. each of) the rows of sensors 137 of the array). The spectra may be compared to the standard spectrum 170 to obtain a correction function, and the like, for correcting the spectra 112. It is understood that the standard spectrum 170 may be obtained using a given illuminating light and that the lamp 125 used with the system 100 to illuminate the line 114 has the same and/or similar spectral properties as the given illuminating light.

As depicted, the memory 118 further stores one or more spectral feature-finding algorithms 180 which may be used by the application 150 to search for spectral features in the spectra 112 which may include, but are not limited to, one or more of: respective locations of peaks of the respective spectra 112; respective magnitudes of the peaks of the respective spectra 112; relative magnitudes of the peaks of the respective spectra 112; slopes of the peaks of the respective spectra 112; respective widths of the peaks of the respective spectra and valleys between the peaks of the respective spectra 112; relative widths of the peaks of the respective spectra 112; a first derivative of the respective spectra 112; a second derivative of the respective spectra 112; spectral peak overlaps of the respective spectra 112; and/or any other suitable spectral feature of the respective spectra 112. Hence, for example, the one or more spectral feature-finding algorithms 180 may include algorithms for finding one or more of peaks, valleys, magnitudes, widths, slopes, and the like in the spectra 112.

Figure 2:
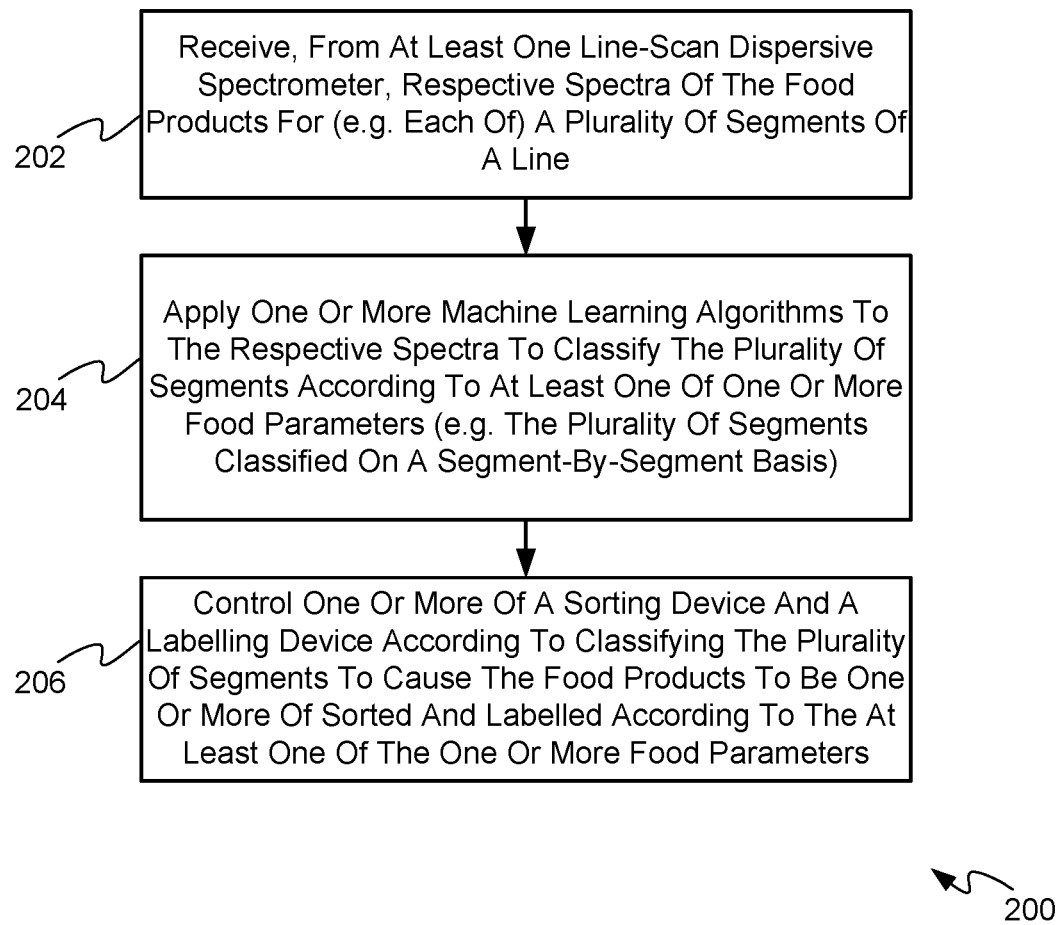
FIG. 2 is a flowchart of a method for one or more of sorting and labeling food products using a line-scan dispersive spectrometer, in accordance with some examples.

Attention is now directed to FIG. 2 which depicts a flowchart representative of a method 200 for one or more of sorting and labeling food products using a line-scan dispersive spectrometer. The operations of the method 200 of FIG. 2 correspond to machine readable instructions that are executed by the device 106 and/or the computing device 126, and specifically the controller 120. In the illustrated example, the instructions represented by the blocks of FIG. 2 are stored at the memory 118 for example, as the application 150. The method 200 of FIG. 2 is one way in which the controller 120 and/or the computing device 126 and/or the device 106 and/or the system 100 may be configured. Furthermore, the following discussion of the method 200 of FIG. 2 will lead to a further understanding of the system 100, and its various components.

The method 200 of FIG. 2 need not be performed in the exact sequence as shown and likewise various blocks may be performed in parallel rather than in sequence. Accordingly, the elements of method 200 are referred to herein as "blocks" rather than "steps." The method 200 of FIG. 2 may be implemented on variations of the system 100 of FIG. 1, as well.

At a block 202, the controller 120 receives, from the at least one line-scan dispersive spectrometer 105, the respective spectra 112 of the food products for (e.g. each of) the plurality of segments 113 of the line 114. (e.g. each of) the spectra 112 may be associated with a respective segment 113, for example based on a row of the array of sensors 137 from which respective spectra 112 are generated and/or based on an order in which the spectra 112 are received and/or based on identifiers of the spectra 112 received with the spectra 112 (e.g. the spectra 112 may include metadata which identifies the spectra 112 as being associated with a particular row of the array of sensors 137 and/or as being associated with a particular segment 113). Hence, a segment 113 may be associated with a particular spectra 112, and vice versa, using any suitable process.

At a block 204, the controller 120 applies the one or more machine learning algorithms 119 to the respective spectra 112 to classify the plurality of segments 113 according to at least one of one or more food parameters. For example, the plurality of segments 113 may be classified on a segment-by-segment basis and/groups of the plurality of segments 113 may be classified, and the like.

Such food parameters may include parameters relating to one or more of food quality and food impurities, which may include, but are not limited to, one or more of:

Food impurities and/or food contaminants such as plastic, safety glove clippings, bone fragments and the like. For example, previously determined line-scan dispersive spectrometer spectra of one or more food impurities and/or food contaminants may be used to train the one or more machine learning algorithms 119 (and/or to generate corresponding classifiers 160 and/or corresponding regressors 161) to classify the spectra 112 according to the presence of food impurities and/or food contaminants.

Food-specific parameters that may be determined based on a type of the food products 101. For example, meat-specific parameters may include protein, fat, lean, bone, cartilage, and the like. However, produce-specific parameters may include skin, stem, seed, flesh, rind, and the like For example, previously determined line-scan dispersive spectrometer spectra of one or more food-specific parameters may be used to train the one or more machine learning algorithms 119 (and/or to generate corresponding classifiers 160 and/or regressors 161) to classify the spectra 112 according to one or more food-specific parameters.

Chemical composition and/or chemical profile and/or chemical indicators of a food product. For example, previously determined line-scan dispersive spectrometer spectra of one or more chemicals related to food may be used to train the one or more machine learning algorithms 119 (and/or to generate corresponding classifiers 160 and/or regressors 161) to classify the spectra 112 according to the one or more chemicals. Such chemicals may include, but are not limited to, chemicals found in meat, poultry, seafood, fruits, vegetables, processed foods and/or any other type of food and/or food contaminants Indeed, such chemicals may include, but are not limited to, chemicals that occur when food is fresh and chemicals that occur when food is not fresh and/or is going bad (e.g. ammonia, and the like).

Amount of sugar, or another specific chemical, of a food product. For example, previously determined line-scan dispersive spectrometer spectra of sugar (or another specific chemical) may be used to train the one or more machine learning algorithms 119 (and/or to generate corresponding classifiers 160 and/or regressors 161) to classify the spectra 112 according to the amount of sugar (or another specific chemical) therein.

pH of a food product. For example, previously determined line-scan dispersive spectrometer spectra of food products having different pH levels may be used to train the one or more machine learning algorithms 119 (and/or to generate corresponding classifiers 160 and/or regressors 161) to classify the spectra 112 according to the different pH levels.

Water content of a food product. For example, previously determined line-scan dispersive spectrometer spectra of food products having different water levels may be used to train the one or more machine learning algorithms 119 (and/or to generate corresponding classifiers 160 and/or regressors 161) to classify the spectra 112 according to the water content.

A water holding capacity of a food product. For example, previously determined line-scan dispersive spectrometer spectra of food products having different water holding capacities may be used to train the one or more machine learning algorithms 119 (and/or to generate corresponding classifiers 160 and/or regressors 161) to classify the spectra 112 according to the water holding capacity. Water holding capacity of a food product may be different from water content of a food product (e.g. water content may indicate a present water content, while water holding capacity may indicate how much water a food product may hold, and how much water may easily escape the food product, regardless of current water content).

A juiciness of a food product. For example, previously determined line-scan dispersive spectrometer spectra of food products having different juiciness levels may be used to train the one or more machine learning algorithms 119 (and/or to generate corresponding classifiers 160 and/or regressors 161) to classify the spectra 112 according to the juiciness. Juiciness of a food product may be different from water content of a food product (e.g. juiciness may be due to liquids different from water and/or binding of such liquids within the food product).

Tenderness of a food product. For example, previously determined line-scan dispersive spectrometer spectra of food products having different tenderness levels may be used to train the one or more machine learning algorithms 119 (and/or to generate corresponding classifiers 160 and/or regressors 161) to classify the spectra 112 according to tenderness.

Color of a food product. For example, previously determined line-scan dispersive spectrometer spectra of food products having different colors may be used to train the one or more machine learning algorithms 119 (and/or to generate corresponding classifiers 160 and/or regressors 161) to classify the spectra 112 according to color.

A physical measurement of a food product (which may include color and/or tenderness, and/or crunchiness, and/or firmness, and/or softness, and/or stretchiness, and/or texture, and the like). For example, previously determined line-scan dispersive spectrometer spectra of food products having different physical measurement (e.g. color, tenderness, crunchiness, firmness, softness, stretchiness, texture and the like) may be used to train the one or more machine learning algorithms 119 (and/or to generate corresponding classifiers 160 and/or regressors 161) to classify the spectra 112 according to a physical measurement.

An integrity measurement of a food product. For example, previously determined line-scan dispersive spectrometer spectra of food products having different integrities may be used to train the one or more machine learning algorithms 119 (and/or to generate corresponding classifiers 160 and/or regressors 161) to classify the spectra 112 according to an integrity measurement. Integrity may be defined, in some examples, as a degree of breakdown of cell membrane in a food products 101, and/or physical destruction of a food product due to cell breakdown with time and/or with handling and/or due to disease. For example, when the food products 101 include spinach, the cell membrane of the spinach breaking down may cause the spinach to be slimy, and the integrity measurement may hence be related to sliminess of the spinach. Similarly, the integrity measurement may be related to wilting, discoloration, spots (e.g. on apples and the like), cuts, broken skin (e.g. on a berry, apple, and the like) disease (e.g. in carrots, potatoes, and the like), insect holes, and the like, of a food product.

A flavor of a food product. For example, previously determined line-scan dispersive spectrometer spectra of one or more flavors may be used to train the one or more machine learning algorithms 119 (and/or to generate corresponding classifiers 160 and/or regressors 161) to classify the spectra 112 according to flavor. Such flavor may be determined using a flavor scale (e.g. as measured using a chemical method and/or determined by experts, described below) and the like, and the one or more machine learning algorithms 119 may be trained to recognized flavor of a food product based on feedback from experts tasting food products, as described below.

A quality of a food product. For example, previously determined line-scan dispersive spectrometer spectra of one or more flavors, and/or of food product color and/or subjective quality grading may be used to train the one or more machine learning algorithms 119 (and/or to generate corresponding classifiers 160 and/or regressors 161) to classify the spectra 112 according to quality. Such quality may be determined using a quality scale, and the like, and the one or more machine learning algorithms 119 may be trained to recognized flavor of a food product based on feedback from experts tasting food products, as described below. It is further understood that quality of a food product may include a combination of one or more of food parameters described herein, and/or any other suitable food parameters related to food quality. For example, food quality may be determined using food parameters that indicate how long a food product may last in a refrigerator (e.g. and/or at a given storage temperature), food parameters that indicate or predict a final result on a user's plate (e.g. when prepared for consumption, such as whether the food product had a pleasant texture, good moisture, expected flavor, etc.), and/or any other suitable food parameters.

It is further understood that different food parameters may be determined in parallel with each other. For example, meat protein at a first pH level may result in different spectra than meat protein at a second pH level; as such, the one or more machine learning algorithms 119 may be trained to classify spectra as protein and according to a pH level. Indeed, a segment 113 classified generically as meat may also be classified according to a specific pH level thereof, for example depending on a mode of the controller 120.

Furthermore, as the plurality of segments 113 may be classified on a segment-by-segment basis, and/or as groups of the plurality of segments 113 may be classified, and the like, and as different segments 113 and/or groups of segments 113 may be classified differently, the one or more machine learning algorithms 119 may be further trained to classify a food product and/or regions of a food product according to classifying groups of the plurality of segments 113 (e.g. groups of the plurality of segments 113 may be considered together). For example, the one or more machine learning algorithms 119 may be further trained to determine a marbling and/or a protein/fat ratio and/or a protein/water ratio of meat, for example, based on relative amounts and/or positions of protein and fat (and/or water) in meat, as determined from classifying the segments 113 individually and amalgamating the results.

Similarly, some physical measurements may be determined from classifying groups of the plurality of segments 111. For example, when the line-scan dispersive spectrometer 105 is acquiring spectra 112 of the segments 113, a first portion of the segments 113 may coincide with a food product 101, while a second portion of the segments 113 may coincide with the conveyor 103; indeed, the one or more machine learning algorithms 119 may be trained to classify spectra 112 of the conveyor 103 so that segments 113 associated with the food product 101 may be distinguished from segments 113 associated with the conveyor 103. Hence, when a resolution (e.g. physical dimensions) of the segments 113 have been stored at the memory 118, the one or more machine learning algorithms 119 may determine physical measurements of the food product 101 (e.g. widths of the food products 101) by determining a length of the first portion of the segments 113. Similarly, as the speed of the conveyor 103 may be known, as is a rate of acquisition of the spectra 112, a length of a food product 101 may be determined based on determining a leading edge and a trailing edge of the food product 101 from the spectra 112.

Hence, in general, it is understood that, at the block 204, the segments 113 may be classified on a segment-by-segment basis and/or that groups of the segments 113 may be classified, and the like. Hence, some segments 113 and/or groups of segments 113 may be classified differently from other segments 113 and/or groups of segments 113; in such examples, the controller 120 may aggregate the classifications to generate an aggregated classification for a food product 101.

In some examples, the controller 120 may be further configured to preprocess at least a portion of the respective spectra 112 by comparing at least a portion of the respective spectra 112 to the at least one standard spectrum 170 and/or by using a correction function derived from the at least one standard spectrum 170 as described above.

In some examples, the controller 120 may be further configured to: preprocess at least a portion of the respective spectra 112 using one or more of the spectral feature-finding algorithms 180 to determine spectral features of the respective spectra 112, the spectral features including one or more of: respective locations of peaks of the respective spectra 112; respective magnitudes of the peaks of the respective spectra 112; relative magnitudes of the peaks of the respective spectra 112; widths of the peaks of the respective spectra 112; relative widths of the peaks of the respective spectra 112; slopes of the peaks of the respective spectra 112; valleys between the peaks of the respective spectra 112; a first derivative of the respective spectra 112; a second derivative of the respective spectra 112; spectral peak overlaps of the respective spectra 112; other spectral features; and classify, using the one or more machine learning algorithms 119, the plurality of segments 113 according to the one or more food parameters based on the spectral features. In other words, the spectral features of the spectra 112 may be determined using the one or more spectral feature-finding algorithms 180 which may be used as input to the one or more machine learning algorithms 119.

Indeed, in some of these examples, the spectral feature-finding algorithms 180 may be used to find peaks that occur between signals from given sensors 137. For example, (e.g. each of) the spectra 112 are generated from a respective row of the sensors 137, which effectively sample the wavelengths of light from a given segment 113; when a peak of the wavelengths do not correspond to a position of a sensor 137 in a row, the spectral feature-finding algorithms 180 may use interpolation techniques, and the like, to find such peaks.

However, such techniques may be applied to any suitable spectral feature. For example, the spectral feature-finding algorithms 180 may be used to find spectral features that occur between signals from given sensors 137. For example, (e.g. each of) the spectra 112 are generated from a respective row of the sensors 137, which effectively sample the wavelengths of light from a given segment 113; when a spectral feature of the wavelengths do not correspond to a position of a sensor 137 in a row, the spectral feature-finding algorithms 180 may use interpolation techniques, and the like, to find such spectral features.

Hence, the raw data of the spectra 112 as received from the line-scan dispersive spectrometer 105 may be preprocessed to search for and/or find such spectral features using interpolation, and the like.

In yet further examples, the controller 120 may be further configured to: determine when a given sensor 137 of the at least one line-scan dispersive spectrometer 105 is one or more of noisy and biased to a given state; and, in response, correct a given respective spectra 112 determined using the given sensor 137, prior to applying the one or more machine learning algorithms 119, using interpolation between respective signals of neighbor sensors 137 of the given sensor 137.

For example, one or more of the sensors 137 may consistently yield a signal of a given value and/or noisy values regardless of food properties of the food products 101, due to a given sensor 137 being noisy and/or malfunctioning, and the like. The one or more machine learning algorithms 119 may be trained to determine when signals from a malfunctioning sensor 137 are one or more of noisy and biased to a given state, and ignore such signals, which causes a gap in a given spectra 112, that may be filled in using interpolation, as based on signals from the sensors 137 neighboring the malfunctioning sensor 137.

At a block 206, the controller 120 controls one or more of the sorting device 107 and the labeling device 109 according to classifying the plurality of segments 113 to cause the food products 101 to be one or more of sorted and labeled according to the at least one of the one or more food parameters. Such sorting and/or labeling may be according to an aggregated classification for a food product 101.

In some examples, the controller 120 may be further configured to: when the respective spectra 112 for a given classification drifts over time, control one or more of the sorting device 107, the labeling device 109 and a notification device (e.g. the notification device 147 and/or another notification device) to provide a notification to cause a calibration of the at least one line-scan dispersive spectrometer 105. For example, the block 204 and/or the block 206 may include tracking spectra 112 that are determined to be of a given classification; due to drift, and the like, in the sensors 137, which may be due to drift in environmental conditions in the food processing facility in which the line-scan dispersive spectrometer 105 is installed. When the drift reaches a threshold level (e.g. which may be included in the application 150), a notification of such may be provided to cause a recalibration of the system 100. Such a recalibration may include obtaining one or more spectra of the standard material 171 used to obtain the standard spectrum 170 to regenerate the calibration function. Alternatively, the block 204 and/or the block 206 may include tracking spectra for the standard material 171 over time to determine the drift (e.g. the light 125 may be periodically used to measure spectra for the standard material 171 to determine drift, manually and/or automatically).

Figure 3:
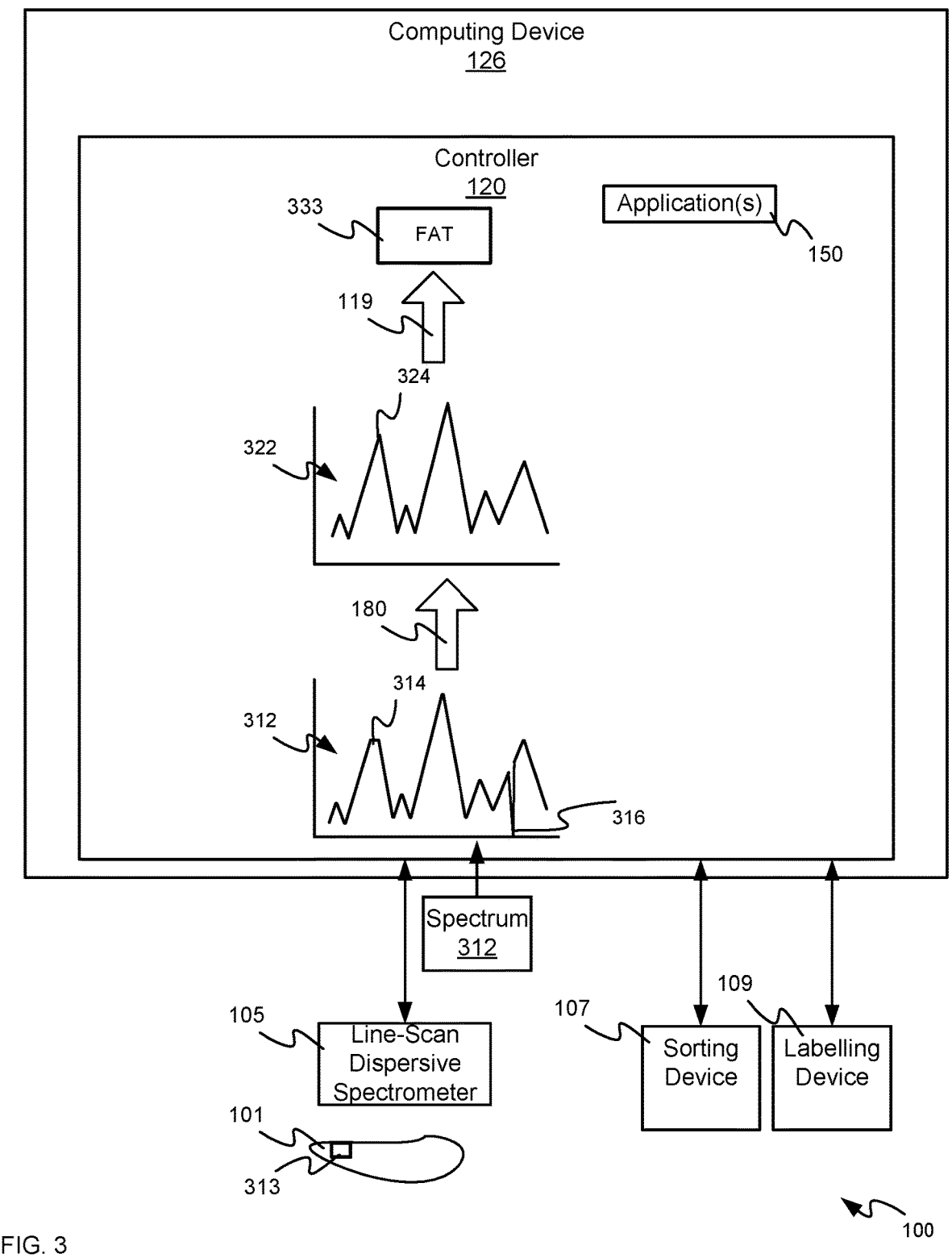
FIG. 3 depicts the system of FIG. 1 implementing a portion of a method for one or more of sorting and labeling food products, in accordance with some examples.
Figure 4:
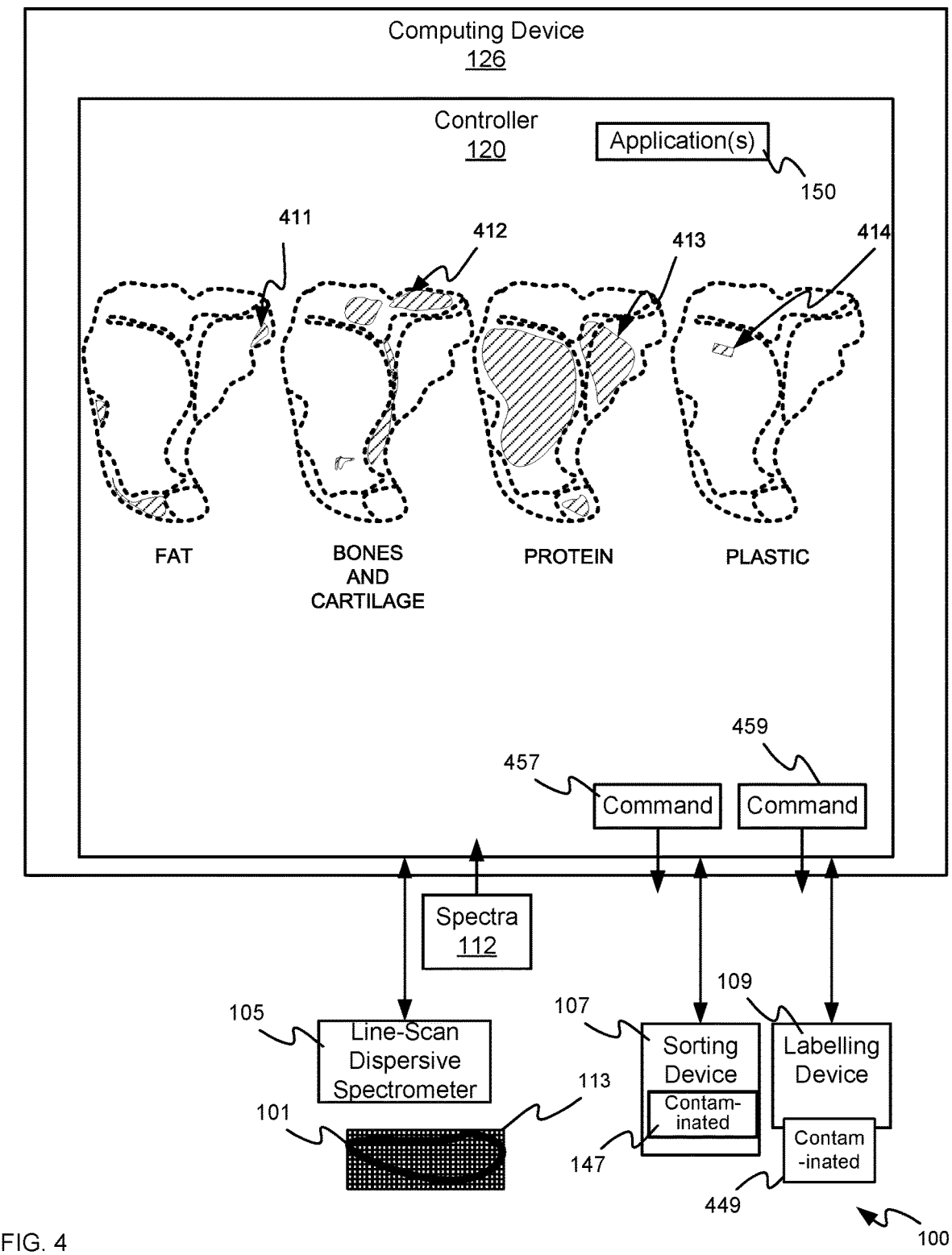
FIG. 4 depicts the system of FIG. 1 implementing another portion of the method for one or more of sorting and labeling food products, in accordance with some examples.

Attention is next directed to FIG. 3 and FIG. 4 which depict the method 200 being implemented in the system 100. While not all components of the system 100 are depicted, they are nonetheless understood to be present. In particular, FIG. 3 and FIG. 4 each depict the controller 120 and/or the computing device 126 in communication with the line-scan dispersive spectrometer 105 (e.g. via the communication interface 122, not depicted), and the controller 120 in communication (e.g. via the communication interface 122) with the sorting device 107 and the labeling device 109 (only one of which may be present).

With reference to FIG. 3, the line-scan dispersive spectrometer 105 has obtained a spectrum 312 (e.g. one of the spectra 112) of a particular segment 313 (e.g. one of the segments 113) corresponding to an area of a food product 101. The spectrum 312 is received at the controller 120 (e.g. at the block 202 of the method 200), which is implementing the application 150. As depicted, the spectrum 312 includes a peak 314 which has a flat top, which may be indicative of an actual local maximum of the peak 314 not corresponding to a position of a sensor 137. Furthermore, the spectrum 312 includes a "0" value 316 which may be indicative of a malfunctioning sensor 137, as described above.

As depicted, the controller 120 preprocesses the spectrum 312 to find an actual maximum of the peak 314, for example using the spectral feature-finding algorithm 180, and further interpolates signals of sensors 137 neighboring the malfunctioning sensor 137 to remove the "0" value 316. As such, an updated spectrum 322 is generated in which a more accurate maximum 324 of the peak 314 is determined, and from which the "0" value 316 is removed.

As depicted, the controller 120 applies the one or more machine learning algorithms 119 to the updated spectrum 322 to classify the segment 313 according to at least one of the one or more food parameters (e.g. at the block 204 of the method 200). For example, as depicted, the controller 120 has generated an indication 333 that the segment 313 has been classified as "FAT".

With reference to FIG. 4, the controller 120 continues to receive spectra 112 for segments 113 that correspond to the food product 101, for example as the food product 101 moves through the line 114, such that a plurality of segments 113 that correspond to the food product 101 may be classified on a segment-by-segment basis and/or groups of the plurality of segments 113 that correspond to the food product 101 may be classified, and the like.

For example, as depicted in FIG. 4, the controller 120 may classify different areas of the food product 101 according to respective spectra 112 that correspond to the areas (e.g. as determined from classified segments 113). As depicted, for example, the controller 120 has classified areas 411, 412, 413, 414 that respectively correspond to segments 113 that have been classified, as fat, bones and cartilage, protein and plastic (e.g. an impurity); in particular, the classified areas 411, 412, 413, 414 of the food product 101 are depicted as shaded regions. FIG. 4 further depicts an outline of the food product 101 around (e.g. each of) the areas 411, 412, 413, 414 to show features of the food product 101 which may be determined from the classification process and/or the spectra 112. For example, spectra 112 which correspond to segments 113 of the line 114 that correspond to regions of the conveyor 103 may be used to determine an outline and/or physical dimensions of the food product 101. As will be described below, in some examples, the system 100, and the like, may include sensing devices other than spectrometers (for example cameras, x-ray devices etc.) and measurement of the food products 113 along the line 113 may also occur using those sensing devices; in these examples, correlation between a position on the food product 101 at a plurality of sensing devices may occur, which may also be used to determine outline and/or physical dimensions of the food product 101.

From the classified areas 411, 412, 413, 414, the controller 120 may control (e.g. at the block 206 of the method 200) one or more of the sorting device 107 and the labeling device 109 according to the classifying to cause the food product 101 to be one or more of sorted and labeled according to the at least one of the one or more food parameters. For example, a protein-to-fat ratio and/or protein-to-lean ratio may be determined and the food product 101 may be sorted according to the ratio, and/or a label may be generated by the labeling device 109 which provides the ratio.

However, as depicted, as the food product 101 includes contamination in the form of plastic (e.g. the area 414). Hence, as depicted, the sorting device 107 is controlled to cause the food product 101 to be sorted as contaminated (e.g. as indicated at the notification device 147), and the labeling device 109 is controlled to generate a label 449 that reads "Contaminated". For example, as depicted, the controller 120 and/or the computing device 126 (and/or the device 106) may transmit a command 457 to the sorting device 107 to cause the sorting device 107 to sort the food product 101 according to the food product 101 being contaminated, and/or the controller 120 and/or the computing device 126 (and/or the device 106) may transmit a command 459 to the labeling device 109 to cause the labeling device 109 to label the food product 101 according to the food product 101 being contaminated.

However, other types of sorting and/or labeling are within the scope of the present specification, for example as based on the classification.

For example, sorting and/or labeling may include, but is not limited to, sorting and/or labeling according to one or more of: the chemical composition of a food product 101, a pH of a food product 101, a water holding capacity of a food product 101, a physical measurement of a food product 101, a fat content of a food product 101, a protein content of a food product 101, a water content of a food product 101, a lean content of a food product 101, a tenderness of a food product 101, a juiciness of a food product 101, a color of a food product 101, an integrity measurement of a food product 101, a flavor (e.g. a current flavor) of a food product 101, marbling of a food product 101, and the like. In some of these examples of the sorting and/or labeling may be for an aggregated classification for a food product 101, such as marbling, and the like.

Furthermore, while the example of FIG. 4 depicts sorting and/or labeling on a piece-wise basis, for example for each food product 101, in other examples sorting and/or labeling may occur on a batch-wise basis. In particular, the food products 101 may comprise small food products, such as blueberries, and the like, which are spread out over the conveyor 103 such that sorting and/or labeling may be challenging on a piece-wise basis; in these examples, batches of the food product 101 may be sorted and/or labels may be generated for batches of the food product 101. For example, sorting and/or labeling may occur for each batch of food products 101 selected by time (e.g. a batch of food products 101 for which the spectra 112 are generated over a given time period, and/or before and/or after a particular classification is determined).

Figure 5:
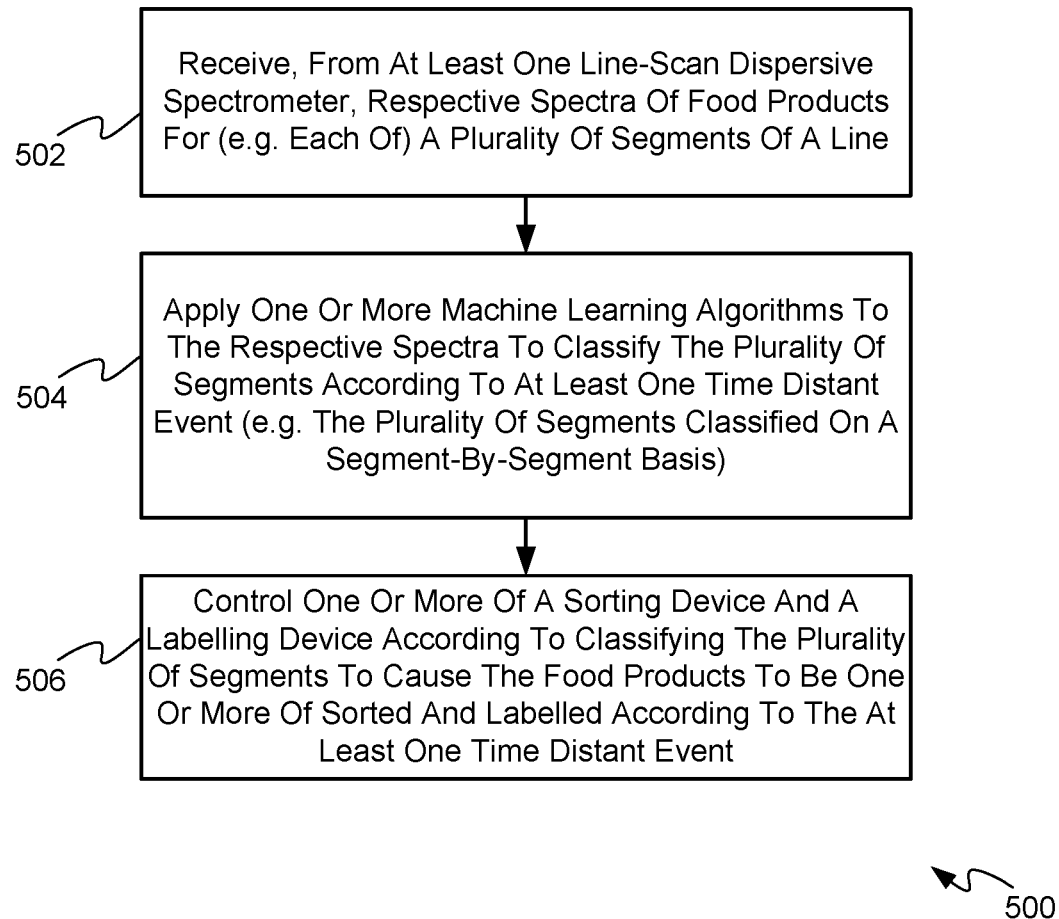
FIG. 5 is a flowchart of a method for one or more of sorting and labeling food products using a line-scan dispersive spectrometer, based on time-distant events, in accordance with some examples.

Attention is now directed to FIG. 5 which depicts a flowchart representative of a method 500 for one or more of sorting and labeling food products according to time-distant events. The operations of the method 500 of FIG. 5 correspond to machine readable instructions that are executed by the device 106 and/or the computing device 126, and specifically the controller 120. In the illustrated example, the instructions represented by the blocks of FIG. 5 are stored at the memory 118 for example, as the application 150. The method 500 of FIG. 5 is another way in which the controller 120 and/or the device 106 and/or the computing device 126 and/or the system 100 may be configured, for example as compared to the method 200. Indeed, the method 200 may represent a first mode in which the controller 120 and/or the device 106 and/or the computing device 126 and/or the system 100 may operate, and the method 500 may represent a second mode in which the controller 120 and/or the device 106 and/or the computing device 126 and/or the system 100 may operate. Alternatively, the method 200 and the method 500 may be implemented simultaneously. Furthermore, the following discussion of the method 500 of FIG. 5 will lead to a further understanding of the system 100, and its various components.

The method 500 of FIG. 5 need not be performed in the exact sequence as shown and likewise various blocks may be performed in parallel rather than in sequence. Accordingly, the elements of method 500 are referred to herein as "blocks" rather than "steps." The method 500 of FIG. 5 may be implemented on variations of the system 100 of FIG. 1, as well.

At a block 502, the controller 120 receives, from the at least one line-scan dispersive spectrometer 105, the respective spectra 112 of the food products for (e.g. each of) the plurality of segments 113 of the line 114. The block 502 is generally similar to the block 202 of the method 200.

At a block 504, the controller 120 applies the one or more machine learning algorithms 119 to the respective spectra 112 to classify the plurality of segments 113 according to at least one time-distant event (e.g. the plurality of segments 113 may be classified on a segment-by-segment basis and/or groups of the plurality of segments 113 may be classified, and the like). The spectra 112 may be pre-processed as described above with respect to the block 204 and/or with respect to FIG. 3. The block 504 is hence generally similar to the block 204 of the method 200.

However, in contrast to the block 204, at the block 504, the controller 120 classifies the plurality of segments 113 according to at least one time-distant event. Hence, in these examples, the one or more machine learning algorithms 119 are trained to classify the segments 113 and/or the spectra 112 according to time-distant events. In some examples, the spectra 112 may also be classified (e.g. via the method 200) according to one or more food parameters related to food quality, food impurities, and the like. In yet further examples, a time-distant event may also be referred to as a type of food parameter.

Such time-distant events may include, but are not limited to, the following:

A geographic location of a source of the food products 101. For example, previously determined line-scan dispersive spectrometer spectra of food products from given geographic locations may be used to train the one or more machine learning algorithms 119 (and/or to generate corresponding classifiers 160 and/or regressors 161) to classify the spectra 112 according to a geographic location. For example, meat from a given farm may yield spectra 112 different from meat from another farm.

A time period that the food products 101 were produced. For example, previously determined line-scan dispersive spectrometer spectra of food products from given time periods (e.g. in a production cycle and/or a time of day and/or a shift) may be used to train the one or more machine learning algorithms 119 (and/or to generate corresponding classifiers 160 and/or regressors 161) to classify the spectra 112 according to a time period. For example, meat produced at a given time of day may yield spectra 112 different from meat produced at another time of day (e.g. due to different levels of stress in live animals being slaughtered which may be due to any of a variety of factors including, but not limited to, specific people working a shift who may treat the animals better or worse than other people, which leads to different chemicals in the meat).

A production method of the food products 101. For example, previously determined line-scan dispersive spectrometer spectra of food products from production methods (e.g. methods of slaughtering an animal for meat, etc.) may be used to train the one or more machine learning algorithms 119 (and/or to generate corresponding classifiers 160 and/or regressors 161) to classify the spectra 112 according to a production method.

A farming method of the food products 101. For example, previously determined line-scan dispersive spectrometer spectra of food products from different farming methods (e.g. organic farming, non-organic farming, early harvests, late harvests, feed mix, etc.) may be used to train the one or more machine learning algorithms 119 (and/or to generate corresponding classifiers 160 and/or regressors 161) to classify the spectra 112 according to a farming method.

A handling method of the food products 101. For example, previously determined line-scan dispersive spectrometer spectra of food products produced using different food handling methods (e.g., manual picking and/or sorting of vegetables at a farm, machine picking and/or sorting of vegetables at a farm, and the like) may be used to train the one or more machine learning algorithms 119 (and/or to generate corresponding classifiers 160 and/or regressors 161) to classify the spectra 112 according to a handling method. For example, manual picking and/or sorting of vegetables of vegetables may result in less bruising than machine picking and/or sorting of vegetables.

A transportation method of the food products 101 from a source of the food products 101 to one or more of a food product sorting facility and a food product labeling facility (e.g. a facility where the system 100 is located). For example, previously determined line-scan dispersive spectrometer spectra of food products transported using different transportation methods may be used to train the one or more machine learning algorithms 119 (and/or to generate corresponding classifiers 160 and/or regressors 161) to classify the spectra 112 according to a transportation method; for example different transportation methods for live animals may lead to different stress levels of the live animals and consequently different chemicals present in meat therefrom.

A storage method of the food products 101 prior to one or more of food product sorting and food product labeling. For example, previously determined line-scan dispersive spectrometer spectra of food products stored using different storage methods may be used to train the one or more machine learning algorithms 119 (and/or to generate corresponding classifiers 160 and/or regressors 161) to classify the spectra 112 according to a storage method; for example food stored in an adequately cooled storage facility may be distinguished from food stored in an inadequately cooled storage facility.

A pre-processing and/or cleaning method of the food products 101 which occurs prior to one or more of the food products 101 sorting and the food products 101 labeling (e.g. at the block 506). For example, previously determined line-scan dispersive spectrometer spectra of food products washed using different processing and/or cleaning methods may be used to train the one or more machine learning algorithms 119 (and/or to generate corresponding classifiers 160 and/or regressors 161) to classify the spectra 112 according to a pre-processing and/or cleaning method. For example, food cleaned with water may be distinguished from food cleaned with other chemicals.

A handling method of the food products 101 which occurs prior to one or more of the food products 101 sorting and the food products 101 labeling. For example, previously determined line-scan dispersive spectrometer spectra of food products handled using different handling methods may be used to train the one or more machine learning algorithms 119 (and/or to generate corresponding classifiers 160 and/or regressors 161) to classify the spectra 112 according to a handling method.

An expiry date of the food products 101. For example, previously determined line-scan dispersive spectrometer spectra of food products having different expiry dates may be used to train the one or more machine learning algorithms 119 (and/or to generate corresponding classifiers 160 and/or regressors 161) to classify the spectra 112 according to an expiry date (e.g. based on a chemical composition determined from the spectra 112). For example, previously determined line-scan dispersive spectrometer spectra of food products whose expiry date has been determined after shipping may be used to train the one or more machine learning algorithms 119 (and/or to generate corresponding classifiers 160 and/or regressors 161) to classify the spectra 112 accordingly to predict an expiry date.

A flavor profile and/or a quality profile of the food products 101 as detectable to a food product consumer after shipment of the food products 101 from one or more of the food products 101 sorting facility and the food products 101 labeling facility. For example, previously determined line-scan dispersive spectrometer spectra of food products whose flavor profile and/or quality profile has been determined after shipping (e.g. and/or after a given time period) by experts (e.g. according to a predetermined rating system) may be used to train the one or more machine learning algorithms 119 (and/or to generate corresponding classifiers 160 and/or regressors 161) to classify the spectra 112 accordingly to predict a flavor profile and/or a quality profile after shipping.

A nutrition profile of the food products 101 after shipment of the food products 101 from one or more of the food products 101 sorting facility and the food products 101 labeling facility. For example, previously determined line-scan dispersive spectrometer spectra of food products having different nutrition profiles after shipping may be used to train the one or more machine learning algorithms 119 (and/or to generate corresponding classifiers 160 and/or regressors 161) to classify the spectra 112 according to a predicted nutrition profile. For example, a nutrition profile may indicate that a food product will be higher in certain vitamins and/or minerals after shipping and/or after a given time period than other food products and/or that a food product will meet a given nutrition profile standard after a given time period (e.g. a food product has at least threshold amounts of certain vitamins and/or minerals, and the like).

A phenotype expression of the food products 101 after shipment of the food products 101 from one or more of the food products 101 sorting facility and the food products 101 labeling facility. For example, previously determined line-scan dispersive spectrometer spectra of food products having different phenotype expressions after shipping (e.g. after a given time period) may be used to train the one or more machine learning algorithms 119 (and/or to generate corresponding classifiers 160 and/or regressors 161) to classify the spectra 112 according to a predicted phenotype expression. For example, a phenotype expression of a food product generally reflects an interaction of the food product with its environment (e.g. after shipping and/or after a given time period).

Hence, the segments 113 may be classified according to past time-distant events and/or predicted, future time-distant events. Furthermore, some future time-distant events may be predicted based on physical and/or chemical analysis of previously produced food products, while other future time-distant events may be predicted based on opinions of experts interacting with (e.g. eating, visual inspection, tactile inspection and the like) previously produced food products; for example, such experts may rate the previously produced food products according to flavor, quality, and the like. Indeed, the predicted flavor and/or quality of a food product by the controller 120 may not indicate a current flavor and/or quality of the food product; rather the predicted flavor and/or quality of a food product by the controller 120 generally indicates a flavor and/or quality of the food product after time has passed (e.g. a time from shipping to serving).

Furthermore, it is understood that, at the block 504, the segments 113 may be classified on a segment-by-segment basis and/or that groups of the segments 113 may be classified, and the like. Hence, some segments 113 and/or groups of the segments 113 may be classified differently from other segments 113 and/or groups of the segments 113 with regards to, for example, flavor and/or quality. Indeed, some segments 113 and/or groups of the segments 113, and the like, (e.g. bones and the like) may not be classified with regards to, for example, flavor and/or quality. In such examples, the controller 120 may aggregate the classifications to generate an aggregated classification for a food product 101.

At a block 506, the controller 120 controls one or more of the sorting device 107 and the labeling device 109 according to classifying the plurality of segments 113 to cause the food products 101 to be one or more of sorted and labeled according to the at least one of the one or more food parameters. Block 506 is generally similar to the block 206 of the method 200, and may include sorting and/or labeling according to an aggregated classification.

As has been referred to above, the one or more machine learning algorithms 119 are generally trained to classify the segments 113. Attention is next directed to FIG. 6 which depicts a portion of the system 100 in a training mode; while not all components of the system 100 are depicted, they are nonetheless understood to be present. Furthermore, the training mode may occur prior to the device 106 and/or the computing device 126 being shipped to a location of the conveyor 103, and/or prior to operating the device 106 and/or the computing device 126 with the line-dispersive spectrometer 105, and/or prior to operating the device 106 and/or the computing device 126 with the line-dispersive spectrometer 105 before a shift at the location of the conveyor 103.

Figure 6:
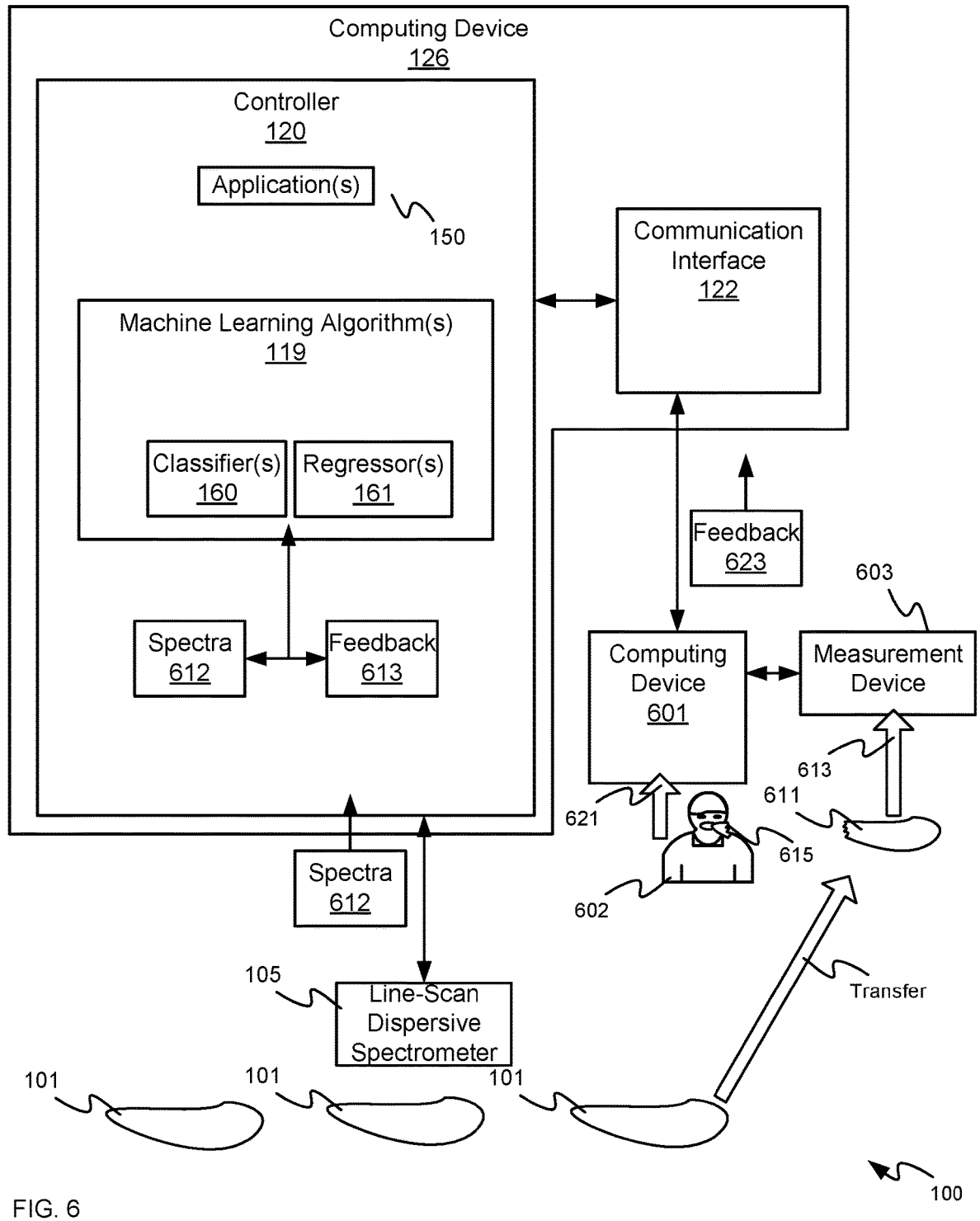
FIG. 6 depicts a portion of the system of FIG. 1 in a training mode, in accordance with some examples.

As depicted in FIG. 6, the controller 120 is in communication with a remote computing device 601 (e.g. different from the device 106 and/or the computing device 126). The computing device 601 may be operated by a user 602 and/or in communication with at least one measurement device 603 configured to measure properties of food products 101, including, but not limited to, physical and/or chemical properties of the food products 101. Furthermore, the user 602 may be an expert in determining flavor profiles and/or quality profiles of the food products 101, and/or the user 602 may be tracking history of the food products 101, including, but not limited to, past time-distant events and/or future time-distant events as described above. Alternatively, the user 602 may include, and/or be replaced by, an artificial intelligence device, and the like, in communication with the at least one measurement device 603, the artificial intelligence device configured to and/or trained to generate expert feedback based on data received from the at least one measurement device 603. The computing device 601 may be local to the user 602 and/or the at least one measurement device 603 and/or the remote computing device 601 may be at least partially located in the cloud, and the like (e.g. the computing device 601 may comprise a cloud computing device). In other examples, the computing device 601 may be at least partially combined with the device 106 and/or computing device 126; for example, the device 106 and/or the computing device 126 may include the computing device 601; and/or the device 106 and/or the computing device 126 may be adapted to include functionality of the computing device 601.

The at least one measurement device 603 may comprise a device configured to measure a food product 101 for one or more of: chemical composition, a pH, a water holding capacity, a fat content, a protein content, a water content, a lean content, a tenderness, a juiciness, a color, an integrity measurement, and the like.

Hence, the at least one measurement device 603 may comprise any suitable combination of chemical and/or physical measurement devices that may quantitatively measure chemical and/or physical properties of food products 101.

The user 602 and/or the at least one measurement device 603 may be located at a same facility as the line-scan dispersive spectrometer 105 and/or another facility.

As depicted, in the training mode, the line-scan dispersive spectrometer 105 is being controlled to obtain spectra 612 (e.g. similar to the spectra 112) of the food products 101, which are received at the controller 120 and, for example, stored at the memory 118 (not depicted in FIG. 6 but nonetheless understood to be present). In particular, the spectra 612 may be stored in a manner that enables a spectrum 612 for a particular food product 101 to be retrieved; for example, the food products 101 may be scanned in a particular order and the spectra 612 saved in a similar order, and/or the food products 101 may be labeled, and the spectra 612 may be stored in association with data identifying such labels, and the like.

As also depicted in FIG. 6, the food products 101 (e.g. after the spectra 612 are obtained) are transferred to the facility where the user 602 and/or the at least one measurement device 603 are located for testing. As depicted, particular food products 611 (e.g. of the food products 101) are being tested by the at least one measurement device 603 to obtain feedback 613, such as chemical and/or physical measurements of the particular food products 611. As also depicted in FIG. 6, the user 602 is tasting the particular food products 611 (e.g. pieces 615 of the particular food products 611, for example before or after cooking the particular food products 611) to determine a flavor and/or a quality profile of the pieces 615.

Alternatively, the user 602 may track a history of the particular food products 611 to determine one or more past and/or future time-distant events associated therewith. In some of the examples, one or more of the particular food products 611 may shipped and/or stored in particular manner that mimics how food products 101 that are processed for commercial use are shipped and/or stored. In some examples, measurement and/or tasting of the particular food products 611 may occur after such shipment and/or storage. Alternatively, tracking history of the particular food products 611 may include accessing an existing database that stores events associated with the particular food products 611 as they are produced and/or processed; in these examples, when the user 602 comprises an artificial intelligence device, the artificial intelligence device may access the existing database to track history of the particular food products 611.

Regardless, the user 602 may provide feedback 621 to the computing device 601 (e.g. via an input device) indicating flavor and/or quality and/or a history of the particular food products 611. One or more of the feedback 613, 621 may be combined by the computing device transmitted as feedback 623 to the controller 120, for example via the communication interface 122. Alternatively, while not depicted in FIG. 6, the feedback 623 may be entered at the input device 124 (e.g. by the user 602 and/or an operator and/or administrator of the system 100). Alternatively, while not depicted in FIG. 6, the feedback 623 may be generated by the artificial intelligence device. Furthermore, the feedback 623 for particular food products 611 may be associated with data identifying labels thereof.

Regardless, the feedback 623 for particular food products 611 is received at the controller 120, associated with respective spectra 612 therefor (e.g. via the data identifying labels), and used to train the one or more machine learning algorithms 119, for example, by updating and/or generating classifiers 160 and/or regressors 161 therefor.

Indeed, the feedback 623 may further include one or more indicators indicating a type of feedback for use in training the one or more machine learning algorithms 119 for specific category classifications. For example, feedback 623 indicating flavor scores may be associated with respective spectra 612 and used to update and/or generate a flavor classifier 160 and/or a flavor regressor 161 used to classify the plurality of segments 113 into categories indicative of flavor using the spectra 112. Similarly, feedback 623 indicating specific chemicals may be associated with respective spectra 612 and used to update and/or generate chemical classifiers 160 and/or regressors 161 used to classify the plurality of segments 113 into categories indicative of the specific chemicals, using the spectra 112. Indeed, the feedback 623 may be used to train the one or more machine learning algorithms 119 to classify the plurality of segments 113 into any suitable category using the spectra 112, for example as described above.

In yet further examples, the one or more food products 611 may be specific food product types, such as protein, fat, bone, cartilage, and the like, which may be used generate the feedback 623 to update and/or generate chemical classifiers 160 and/or regressors 161 used to classify the plurality of segments 113 into associated categories, using the spectra 112.

In yet further examples, the computing device 601 may store copies of the one or more machine learning algorithms 119, and the spectra 612 may be transmitted to the computing device 601 by the controller 120 via the communication interface 122. In these examples, the computing device 601 may train copies of the one or more machine learning algorithms 119 for example by generating classifiers and/or regressors therefor based on the feedback 613, 621. Hence, in such examples, the feedback 623 may include one or more classifiers 160 and/or regressors 161 that are transmitted to the controller 120 for storage at the memory 118 such that the one or more machine learning algorithms 119 may use such classifiers 160 and/or regressors 161 classify the plurality of segments 113 into associated categories indicative of food parameters, and the like (e.g. as described above), using the spectra 112. In other words, in these examples, training of the one or more machine learning algorithms 119 may occur in the cloud and/or at a computing device external to the facility where the line-scan dispersive spectrometer 105 is located. Specific examples of such cloud-based training of machine learning algorithms is described below with respect to FIG. 14, FIG. 15 and FIG. 16.

While the system 100 has been described heretofore as including the line-scan dispersive spectrometer 105, in other examples, the system 100 may include and/or be adapted to include other types of line-scan sensing devices and/or line-scan imaging devices which acquire sensed data and/or images along a line including, but not-limited to, line-scan cameras (e.g. cameras that acquire images of food products along a line), line-scan x-ray devices (e.g. x-ray devices that measure a food product using x-rays along a line), line-scan magnetic resonance imaging (e.g. MRI devices that acquire MRI images of a food product along a line). Indeed, line-scan sensing devices may enable more data and/or detail of a food product to be acquired than non-line-scan sensing devices for example by controlling a speed of the conveyor 103 relative to a rate of data collection of a line-scan sensing device. Such line-scan sensing devices may be used in place of the line-scan dispersive spectrometer 105, and/or be used in addition to the line-scan dispersive spectrometer 105.

Furthermore, as will be described hereafter, when the system 100 is adapted to include a first sensing device that acquires first sensed data along a first sensed line, and the one or more machine learning algorithms 119 have been trained to classify a plurality of first segments of the first line into categories indicative of one or more food parameters, such classifications may be used to train the one or more machine learning algorithms 119 to classify a plurality of second segments of a second line measured by a second sensing device into categories indicative of the one or more food parameters, assuming that the first line and the second line each correspond to a common sensed line at food products.

Figure 7:
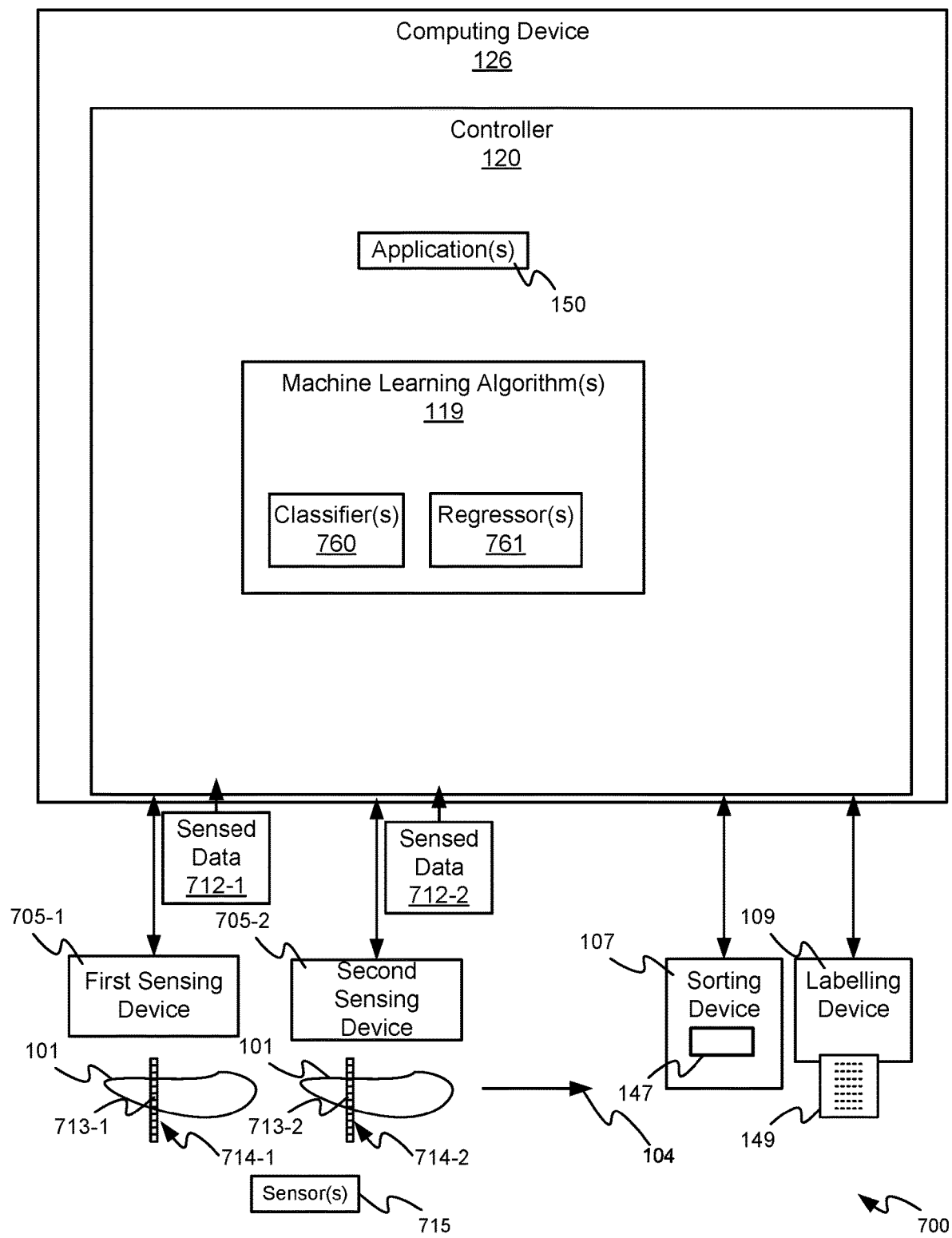
FIG. 7 depicts is a schematic view of a device and system for one or more of sorting and labeling food products using two sensing devices, in accordance with some alternative examples.

For example, attention is next directed to FIG. 7 which depicts a system 700 which is substantially similar to the system 100, with like components having like numbers including, but not limited to, the computing device 126. However, while FIG. 7 does not show all components thereof, it is understood, for example, that the memory 118 and the communication interface 122 (and optionally the device 106) are present in the system 700, with the communication interface 122 configured to communicate with other components of the system 700.

However, in contrast to the system 100, the system 700 is modified to include a first sensing device 705-1 configured to acquire respective first sensed data 712-1 of the food products 101 for (e.g. each of) a plurality of first segments 713-1 of a first line 714-1.

For example, the first sensing device 705-1 may comprise the line-scan dispersive spectrometer 105, and the respective first sensed data 712-1 may comprise the respective spectra 112 of the food products 101; similarly, the plurality of first segments 713-1 and the first line 714-1 may respectively comprise the plurality of segments 113 and the line 114.

In further contrast to the system 100, the system 700 further comprises a second sensing device 705-2 configured to acquire respective second sensed data 712-2 of the food products 101 for (e.g. each of) a plurality of second segments 713-2 of a second line 714-2. In some examples, as depicted the system 700 may further comprise one or more optional sensors 715 for detecting one or more of conveyor speed and positions of the food products 101. As depicted, the second sensing device 705-2 is located further along the food product path direction 104 than the second sensing device 705-2, and data acquisition of the first sensed data 712-1 and the second sensed data 712-2 is coordinated with the speed of the conveyor 103 for example as determined using a conveyor speed sensor and/or a preconfigured conveyor speed, such that the first sensed data 712-1 and the second sensed data 712-2 are (e.g. each of) the same and/or similar regions of a food product 101. Alternatively, a position sensor may detect positions of the food products 101 to coordinate data acquisition of the sensing devices 705-1, 705-2. Put another way, the first line 714-1 and the second line 714-2 each correspond to a common sensed line (and/or a common linear region and/or a common spatial region) at the food products 101. However, while the lines 714 are each depicted as being about perpendicular to the food product path direction 104, the lines 714 may be at different angles to the food product path direction 104, with the sensing devices 705 calibrated such that the first segments 713-1 of the first line 714-1 are registered to, and/or associated with, the second segments 713-2 of the second line 714-2. Furthermore, the segments 713-1, 713-2 need may the same or different resolutions; when the segments 713-1, 713-2 have different resolutions, any suitable interpolation technique may be used to interpolate the segments 713 of the smaller resolution to registered, and/or associated, the segments 713 with second segments 713 having the larger resolution.

In yet further examples, (e.g. each of) the sensing devices 705-1, 705-2 (interchangeably referred to hereafter, collectively, as the sensing devices 705 and, generically, as a sensing device 705) may be configured to collect respective sensed data 712-1, 712-2 along respective lines 714-1, 714-2 simultaneously; for example, the sensing devices 705 may be optically joined via suitable optics including any suitable combination of mirrors, beam splitters, beam combiners, dichroics, prisms, and the like such that the respective lines 714-1, 714-2 coincide and light from the common sensed line (e.g. coincidental lines 714-1, 714-2) is directed to (e.g. each of) the sensing devices 705.

In some examples, the second sensing device 705-2 comprises a line-scan camera and the respective second sensed data 712-2 comprises line-scan images of the food product 101. However, (e.g. each of) the sensing devices 705 may comprise any suitable sensing device configured to acquire respective sensed data of food products for (e.g. each of) a respective plurality of segments of a respective line, with the respective sensed data depending on the underlying technology and/or a type of a respective sensing device.

Indeed, depending on a type of sensing device, the respective segments for which sensed data is acquired may be two-dimensional (e.g. pixels) or three-dimensional (e.g. voxels). For example, when a sensing device 705 comprises the line-scan dispersive spectrometer 105, a line-scan camera, and the like, respective segments of a respective line may be two-dimensional; however, when a sensing device 705 comprises a line-scan MRI device, and the like, respective segments of a respective line may be three-dimensional.

As depicted, the one or more machine learning algorithms 119 (e.g. as stored at the memory 118, not depicted) are trained to classify the plurality of first segments 713-1 into categories indicative of one or more food parameters. For example, as depicted, the one or more machine learning algorithms 119 include classifiers 760 and/or regressors 761, which may be similar to, and/or the same as, the classifiers 160 and/or regressors 161, as described above, and applied to the respective first sensed data 712-1 to classify the plurality of first segments 713-1 according to at least one food parameter and/or time-distant event, as also described above.

As will be described hereafter, the first sensed data 712-1 and the classifiers 760 and/or regressors 761, as well as the second sensed data 712-2, may be used to train the one or more machine learning algorithms 119 to also classify the plurality of second segments 713-2 according to at least one food parameter and/or time-distant event to sort and/or label food products.

Hence, by now it is apparent that the system 700 may comprise the system 100 modified to include the sensing devices 705. Furthermore, the device 106 may be modified to include both or all of the sensing devices 705.

Figure 8:
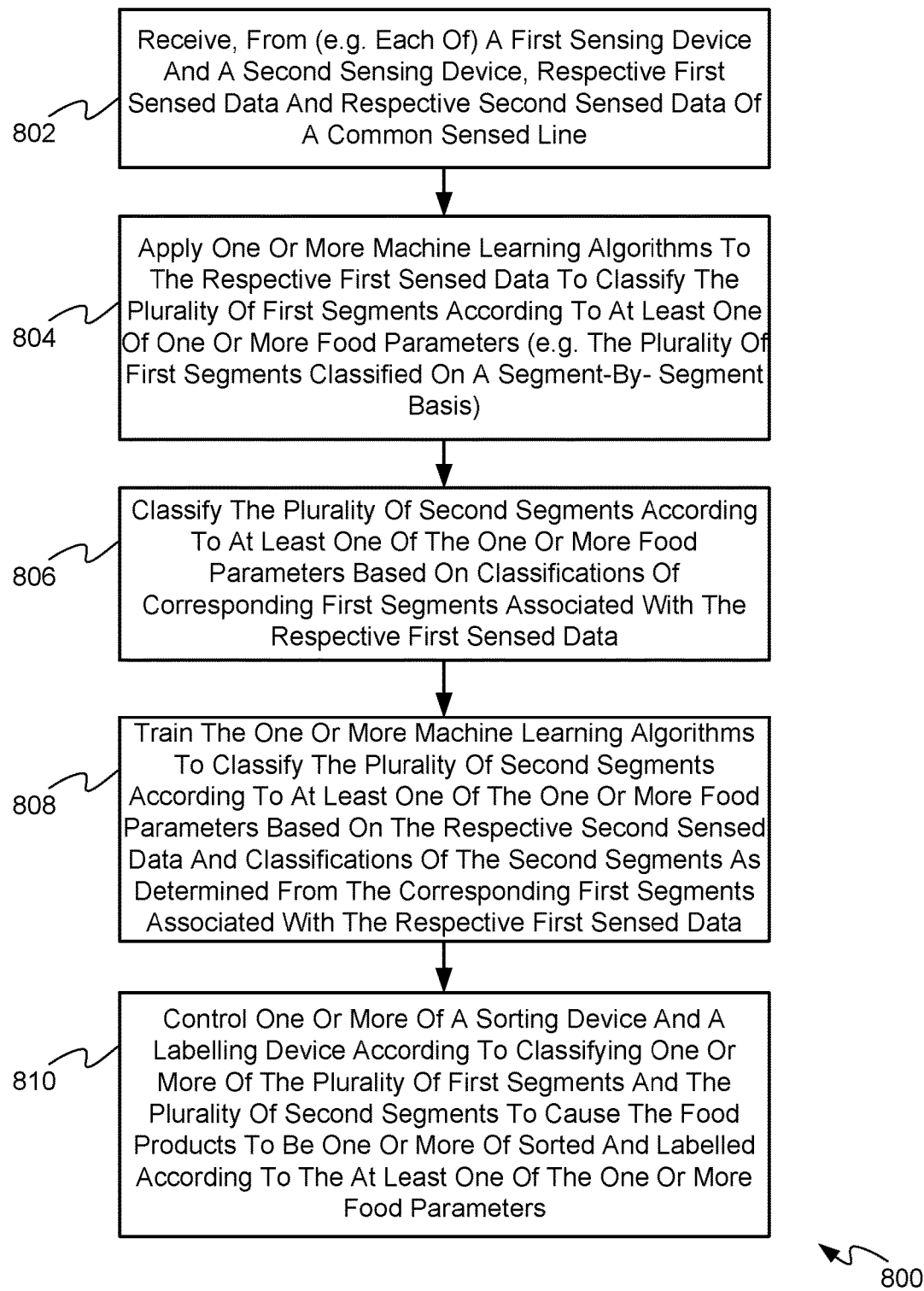
FIG. 8 is a flowchart of a method for one or more of sorting and labeling food products including cross-training of machine-learning algorithms using two sensing devices, in accordance with some examples.

Attention is now directed to FIG. 8 which depicts a flowchart representative of a method 800 for one or more of sorting and labeling food products including cross-training of machine-learning algorithms using two sensing devices. The operations of the method 800 of FIG. 8 correspond to machine readable instructions that are executed by the device 106 and/or the computing device 126, and specifically the controller 120. In the illustrated example, the instructions represented by the blocks of FIG. 8 are stored at the memory 118 for example, as the application 150. The method 800 of FIG. 8 is another way in which the controller 120 and/or the device 106 and/or the computing device 126 and/or the system 100 may be configured, for example as compared to the method 200 and the method 500. Indeed, the methods 200, 500, and 800 may respectively represent a first, second and third modes in which the controller 120 and/or the device 106 and/or the computing device 126 and/or the systems 100, 700 may operate. Furthermore, the following discussion of the method 800 of FIG. 8 will lead to a further understanding of the system 700 and/or the system 100, and its various components.

The method 800 of FIG. 8 need not be performed in the exact sequence as shown and likewise various blocks may be performed in parallel rather than in sequence. Accordingly, the elements of method 800 are referred to herein as "blocks" rather than "steps." The method 800 of FIG. 8 may be implemented on variations of the system 700, and or/the system 100 as well.

At a block 802, the controller 120 receives, from (e.g. each of) the first sensing device 705-1 and the second sensing device 705-2, the respective first sensed data 712-1 and the respective second sensed data 712-2 of a common sensed line (e.g. the lines 714-1, 714-2). Indeed, the block 802 is similar to the block 202 of the method 200, but implemented for both the sensing devices 705 and both sets of sensed data 712-1, 712-2.

At a block 804, the controller 120 applies the one or more machine learning algorithms 119 to the respective first sensed data 712-1 to classify the plurality of first segments 713-1 according to at least one of one or more food parameters (which may include time-distant events), the plurality of first segments 713-1 (e.g. classified on a segment-by-segment basis and/or groups of the first segments 713-1 may be classified, and the like). Indeed, the block 802 is similar to the block 204 of the method 200, as applied to the first sensed data 712-1.

At a block 806, the controller 120 classifies the plurality of second segments 713-2 according to at least one of the one or more food parameters based on classifications of corresponding first segments 713-1 of the respective first sensed data 712-1. For example, when a segment 713-1 is classified as "FAT" and/or as having a particular flavor (e.g. using a classifier 760 and/or regressor 761 corresponding to fat, and/or a classifier 760 and/or a regressor 761 corresponding to the particular flavor) a corresponding segment 713-2 may also be classified as "FAT" or as having the particular flavor.

At a block 808, the controller 120 trains the one or more machine learning algorithms 119 to classify the plurality of second segments 713-2 according to at least one of the one or more food parameters based on the respective second sensed data 712-2 and classifications of the second segments 713-2 as determined from the corresponding first segments 713-1 associated with the respective first sensed data 712-1. Hence, for example, respective classifiers for the second sensed data 712-2 may be generated that correspond to a same and/or similar classification as a classifier 760 and/or regressor 761 used to classify a segment 713-1.

However, as the sensing devices 705 may generally be of different types, the features in the second sensed data 712-2 that may correspond to a given classification are generally different from respective features in the first sensed data 712-1 that correspond to the given classification. For example, when the first sensed data 712-1 comprises the spectra 112, respective given features of the first sensed data 712-1 that correspond to a given classification may be spectral features (e.g. peaks, etc., as described above), whereas when the second sensed data 712-2 comprises line images (e.g. from a line camera), the given features of the second sensed data 712-2 that correspond to a given classification may be image features or 3D features (e.g. particular colors, shading, optical density, presence and magnitude of magnetic dipoles etc.).

Hence, when the first sensing device 705-1 and the second sensing device 705-2 comprise different sensing device types, the one or more machine learning algorithms 119 may be trained to classify the respective first sensed data 712-1 and the respective second sensed data 712-2 based on different respective features of (e.g. each of) the respective first sensed data 712-1 and the respective second sensed data 712-2.

In general, prior to implementing the block 808, and/or in conjunction with implementing the block 808, the controller 120 generally determines correspondences between the segments 713-1, 713-2. For example, when the segments 713-1, 713-2 are (e.g. each of) a similar size and/or length, and/or shape, the controller 120 may determine that the segments 713-1, 713-2 correspond on one-to-one basis based on respective positions of the segments 713-1, 713-2 in the respective lines 714-1, 714-2.

However, in other examples, the first sensing device 705-1 and the second sensing device 705-2 may have different segment resolutions. For example, the first segments 713-1 may be of a different size and/or length, and/or shape as the second segments 713-2. In these examples, the plurality of first segments 713-1 and the plurality of second segments 713-2 have different segment resolutions, and the controller 120 may be further configured to determine correspondences between the plurality of first segments 713-1 and the plurality of second segments 713-2 prior to classifying (e.g. at the block 808) the plurality of second segments 713-2 associated with the respective second sensed data 712-2 according to the at least one of the one or more food parameters based on the classifications of the corresponding first segments 713-1 associated with the respective first sensed data 712-1.

For example, such correspondences may also be determined based on respective positions of the segments 713-1, 713-2 in the respective lines 714-1, 714-2, but may not generally be on a one-to-one basis.

At a block 810, the controller 120 controls one or more of the sorting device and the labeling device according to classifying one or more of the plurality of first segments 713-1 and the plurality of second segments 713-2 to cause the food products to be one or more of sorted and labeled according to the at least one of the one or more food parameter. Indeed, the block 810 is similar to the block 206 of the method 200, but implemented using one or both of the classifying of the plurality of first segments 713-1 and the classifying of the plurality of second segments 713-2.

Hence, the method 800 may be used to train the one or more machine learning algorithms 119 to classify data acquired by the second sensing device 705-2, for example after the one or more machine learning algorithms 119 has been trained classify data acquired by the first sensing device 705-1. Hence, for example, the system 700 may initially operate using only the first sensing device 705-1, and the second sensing device 705-2 may be added at a later time, with training of the one or more machine learning algorithms 119 to classify sensed data acquired by the second sensing device 705-2 occurring automatically, for example in-situ in a food sorting facility and/or a food labeling facility and/or a food processing facility.

Indeed, such training may be extended to a third sensing device (and/or more sensing devices) added to the system 700 and/or the device 106, for example between the sensing devices 705 and/or after or before the sensing devices 705 along the food product path direction 104.

For example, the system 700 and/or the device 106 may be expanded to further comprise a third sensing device configured to acquire respective third sensed data of the food products 101 for (e.g. each of) a plurality of third segments arranged along a third line corresponding to the common sensed line at the food products 101. The controller 120 may be placed into a training mode to: receive, from the third sensing device, the respective third sensed data of the common sensed line; apply the one or more machine learning algorithms 119 to one or more of the respective first sensed data 712-1 and the respective second sensed data 712-1 to classify one or more of the plurality of first segments 713-1 and the plurality of second segments 713-2 according to at least one of one or more food parameters; classify the plurality of third segments of the respective third sensed data according to at least one or more food parameters based on classifications of one or more of the corresponding first segments 713-1 associated with the respective first sensed data 712-1 and corresponding second segments 713-2 associated with the respective second sensed data 712-2; train the one or more machine learning algorithms 119 to classify the plurality of third segments according to at least one of the one or more food parameters based on the respective third sensed data and classifications of the plurality of third segments as determined from one or more of the corresponding first segments 713-1 associated with the respective first sensed data 712-1 and corresponding second segments 713-2 associated with the respective second sensed data 712-2; and control the notification device according to classifying one or more of the plurality of first segments 713-1, the plurality of second segments 713-2 and the plurality of third segments to cause the food products 101 to be one or more of sorted and labeled according to the at least one of the one or more food parameters. In some examples, one or more of the plurality of first segments 713-1 and the plurality of second segments 713-2 may be classified on a segment-by-segment basis. In other examples, one or more of first groups of the plurality of first segments 713-1 and second groups of the plurality of second segments 713-2 may be classified.

Indeed, any suitable number of sensing devices may be added to the system 700 and/or the system 100, and the one or more machine learning algorithms 119 may be trained accordingly as long as one of the sensing devices has been previously trained.

Figure 9:
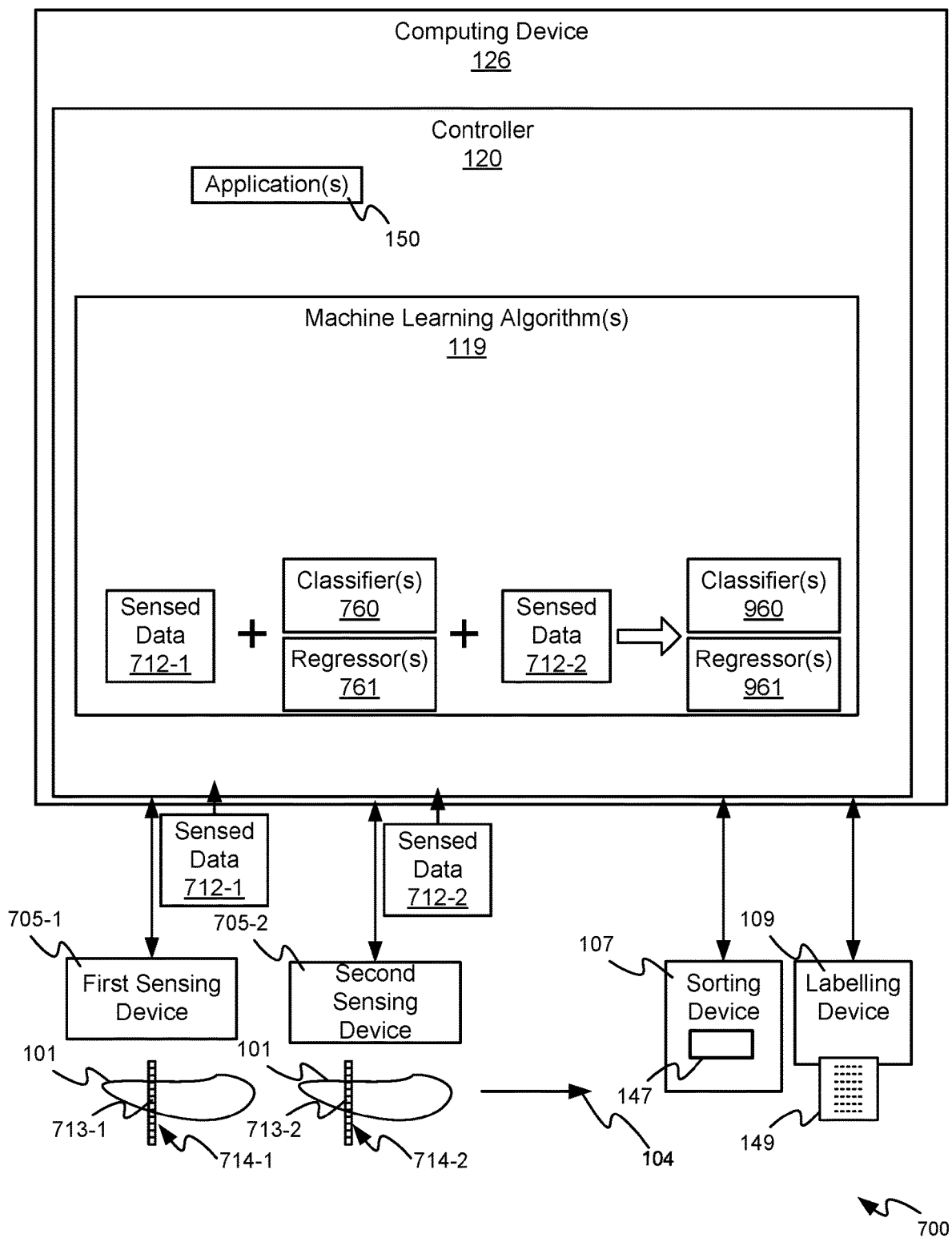
FIG. 9 depicts the system of FIG. 7 implementing a portion of a method for one or more of sorting and labeling food products including cross-training of machine-learning algorithms on two sensing devices, in accordance with some examples.

Attention is next directed to FIG. 9, which is substantially similar to FIG. 7, with like components having like numbers. Specifically, FIG. 9 depicts a portion of the method 800 being implemented. As depicted, in FIG. 9, the controller 120 is training the one or more machine learning algorithms 119 to classify the plurality of second segments 713-2. In particular, in FIG. 9, the controller 120 has input the sensed data 712-1, 712-2 to the one or more machine learning algorithms 119 which classifies the first sensed data 712-1 (and hence respective segments 713-1) using the classifiers 760 and/or the regressors 761. Correspondences between the first sensed data 712-1 and the second sensed data 712-2 are determined, for example based on correspondences between the segments 713-1, 713-2 to classify the second sensed data 712-2 similar to corresponding first sensed data 712-1. In particular, classifiers 960 and/or regressors 961 associated with the second sensed data 712-2 are generated which may be used to classify the second sensed data 712-2. Hence, for example, when a given classifier 760 and/or a given regressor 761 is used to identify fat and/or a particular flavor in a first segment 713-1 using first sensed data 712-1 (e.g. a spectrum 112) of the first segment 713-1, a corresponding given classifier 960 and/or a corresponding given regressor 961 may be generated which may be used to also identify fat and/or the particular flavor in a second segment 713-2 using the second sensed data 712-2 (e.g. images of a second segment 713-2).

In some examples, the one or more machine learning algorithms 119 may be trained to identify unknown features of sensed data.

Figure 10:
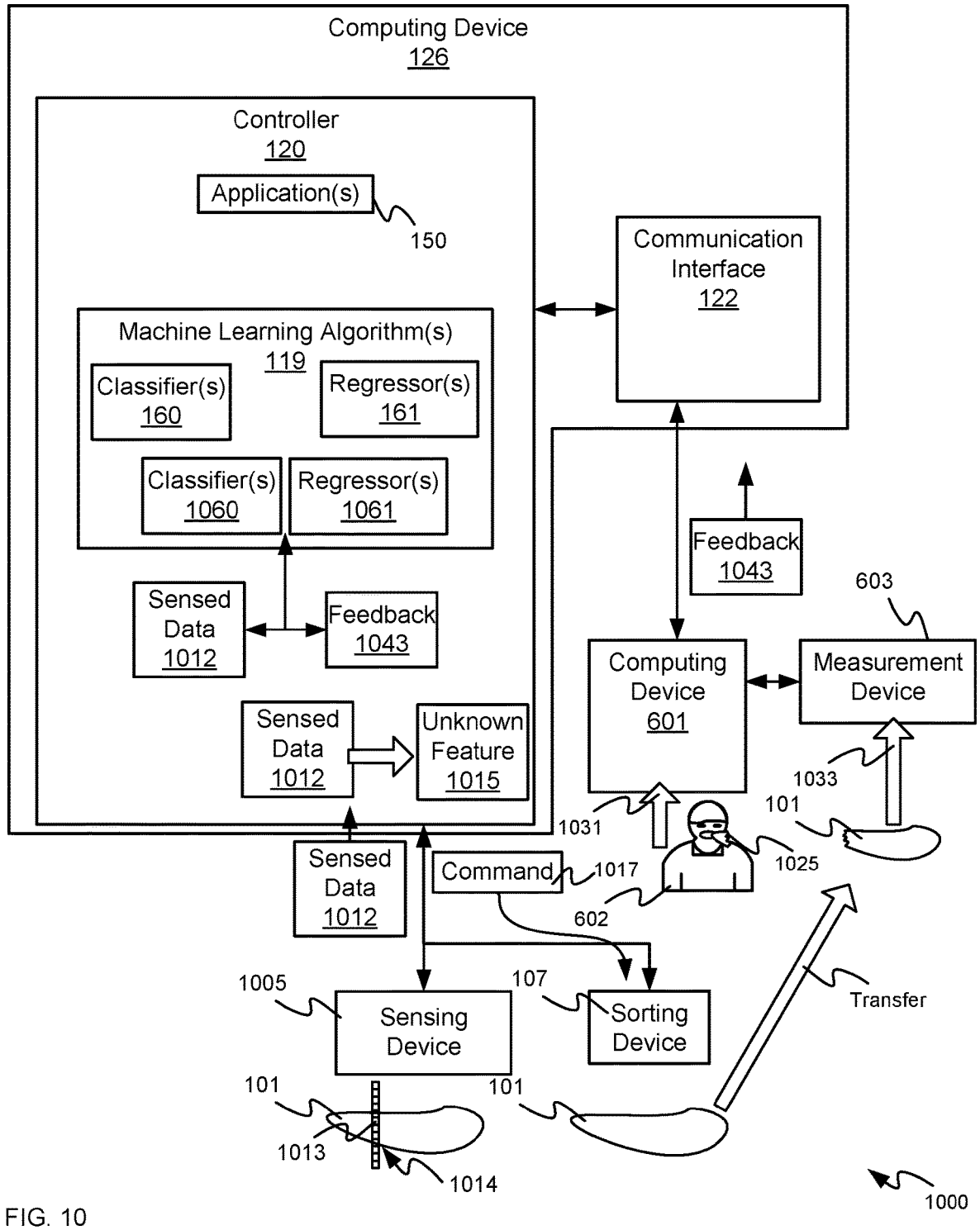
FIG. 10 depicts is a schematic view of a device and system for one or more of sorting and labeling food products using a sensing device, the device and system being depicted in a training mode to recognize unknown features, in accordance with some alternative examples.

For example, attention is next directed to FIG. 10 which depicts a system 1000 which is substantially similar to the system 100 and/or the system 700, with like components having like numbers including, but not limited to, the computing device 126. However, while FIG. 10 does not show all components thereof, it is understood, for example, that the memory 118 and the communication interface 122 (and optionally the device 106) are present in the system 1000, with the communication interface 122 configured to communicate with other components of the system 1000.

In contrast to the system 700, the system 1000 is depicted with only one sensing device 1005 which may comprise any of the sensing devices 705 and/or the line-scan dispersive spectrometer 105. Furthermore, the device 106 may be modified to include the one sensing device 1005.

In particular, the sensing device 1005 is configured to acquire respective sensed data 1012 of the food products 101 for (e.g. each of) a plurality of segments 1013 arranged along a line 1014. In these examples, the controller 120 may be configured to: receive, from the sensing device 1005, the respective sensed data 1012 of the food products 101 for (e.g. each of) the plurality of segments 1013 of the line 1014; apply the one or more machine learning algorithms 119 to the sensed data 1012 to classify the plurality of segments 1013 according to at least one of one or more food parameters; identify, from the respective sensed data 1012, an unknown feature not recognized by the one or more machine learning algorithms 119; control one or more of the sorting device 107 and the labeling device 109 to cause one or more of sorting and labeling of a respective food product 101 at which the unknown feature was detected; receive, via the communication interface 122, feedback to classify the unknown feature as a learned feature; and update the one or more machine learning algorithms 119 to classify the plurality of segments 1013 according to the learned feature such that respective segments of further sensed data 1012 of further food products 101 are classified according to one or more of the learned feature and at least one of the one or more food parameters. In some examples, the plurality of segments 1013 may be classified on a segment-by-segment basis. In other examples, groups of the plurality of segments 1013 may be classified.

For example, as depicted, sensed data 1012 for a particular food product 101 is received at the controller 120; and the controller 120 uses the one or more machine learning algorithms 119 to attempt to classify the segment 1013 from which the sensed data 1012 was obtained, for example using the classifiers 160 and/or regressors 161. However, as depicted, the controller 120 may not be able to classify the segment 1013 from which the sensed data 1012 was obtained and determines that the sensed data 1012 includes an unknown feature 1015.

The sorting device 107 (and/or the labeling device 109) may be controlled (e.g. via a command 1017, and the like) to cause the particular food product 101 from which the sensed data 1012 was obtained to be transferred to the facility where the user 602 and/or the at least one measurement device 603 is located for analysis.

The user 602 may taste or otherwise inspect a piece 1025 of the particular food product 101 and/or the at least one measurement device 603 may be used to analyze and/or measure the particular food product 101, as described above, to respectively obtain feedback 1031 (similar to the feedback 621) and/or feedback 1033 (similar to the feedback 613) which may be transmitted as feedback 1043 (similar to feedback 623) to the controller 120 via computing device 601 and the communication interface 122 (and/or received via the input device 124). The feedback 1033 may be used, in conjunction with the respective sensed data 1012 of the particular food product 101 from which the respective sensed data 1012 was obtained, to train the one or more machine learning algorithms 119 to recognize the unknown feature 1015 as a learned feature; for example, a new classifier 1060 may be generated from the combination of the respective sensed data 1012 and the feedback, the new classifier 1060 for use by the one or more machine learning algorithms 119 in classifying the sensed data 1012 according to the learned feature. Thereafter, respective segments 1013 associated with further sensed data 1012 of further food products 101 may be classified according to one or more of the learned features and at least one of the one or more food parameters.

For example, when the sensing device 1005 comprises the line-scan dispersive spectrometer 105, the sensed data 1012 may comprise the spectra 112, and the unknown feature 1015 may comprise one or more peaks and/or spectral features which does not correspond to any peaks and/or spectral features recognized by the one or more machine learning algorithms 119 as corresponding to a food parameter.

In particular, when the sensing device 1005 comprises the line-scan dispersive spectrometer 105, and the sensed data 1012 comprises the spectra 112, the controller 120 may find spectral features in the spectra 112 that do not correspond to any "known" food parameters. Such spectral features, such as known peaks, and the like, may represent a new type of food parameter, such as a new flavor, a new chemical, a new type of contaminant, a new type of time-distant event (e.g. a new food handling technique being employed at a farm producing the food products 101), and the like. The food product 101 from which the unknown spectral features were acquired may be sorted from the other food products 101 via the sorting device 107 and transferred to the facility where the at least one measurement device 603 and/or the user 602 is located for analysis. The analysis may identify, for example, a new type of food parameter (e.g. a new contaminant and/or a new type of chemical) which may be identified in the feedback 1033. The user 602 may investigate the history of the analyzed food product 101 and/or taste the analyzed food product 101 to determine a flavor score and/or quality score, and the like of the analyzed food product 101, which may also be identified in the feedback 1031. The combined feedback 1043 (which may comprise one or both of the feedback 1031, 1033) may be provided to the controller 120 as the feedback 1043 and used to update and/or train the one or more machine learning algorithms 119 to identify the unknown feature 1015 in further food products 101 and classify the unknown feature 1015 according to a food parameter identified in the feedback 1043, such that the unknown feature 1015 becomes a learned feature identifiable via the classifier 1060.

Figure 11:
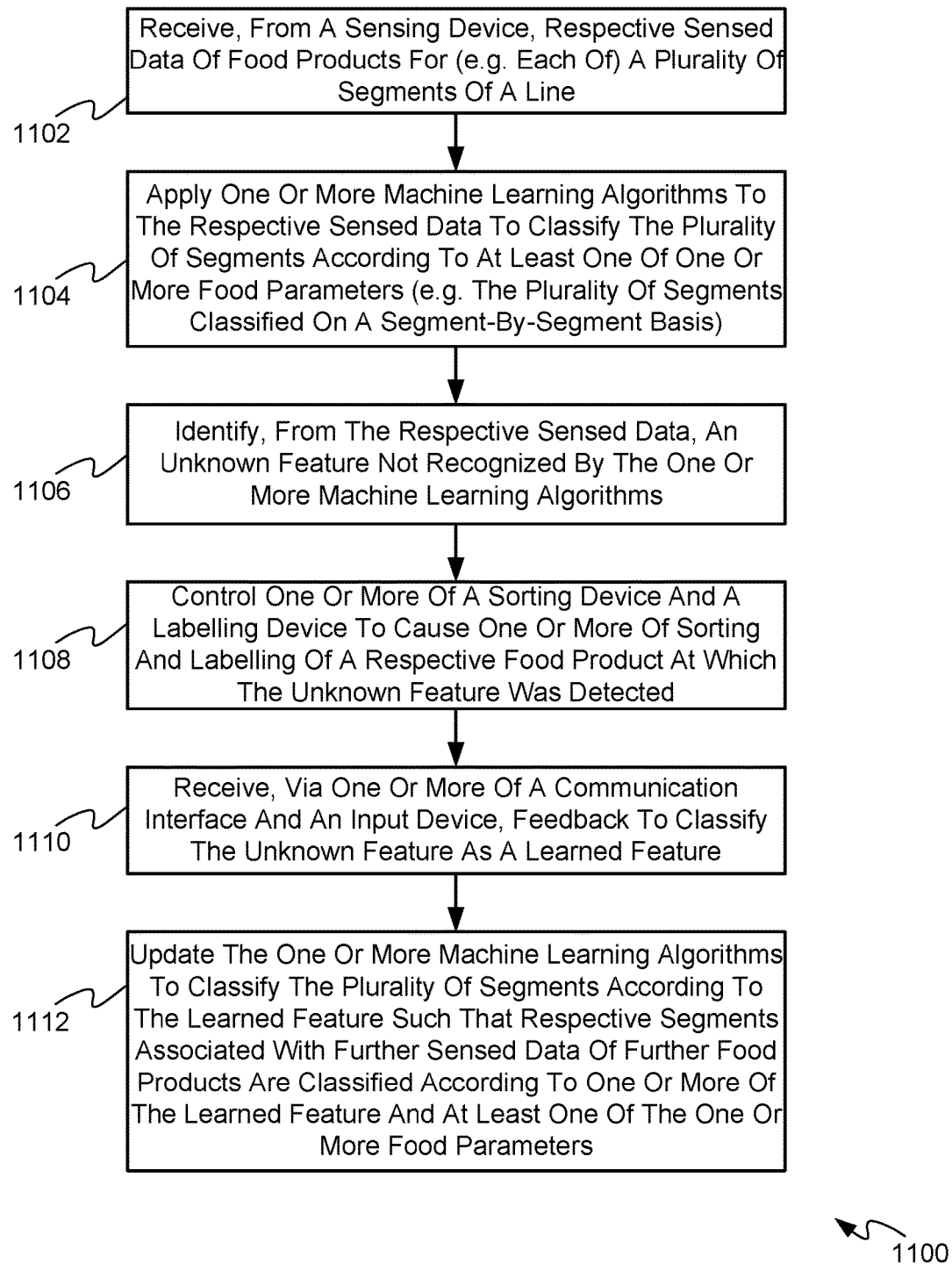
FIG. 11 is a flowchart of a method for one or more of sorting and labeling food products including training of machine-learning algorithms to recognize unknown features, in accordance with some examples.

Indeed, attention is now directed to FIG. 11 which depicts a flowchart representative of a method 1100 for one or more of sorting and labeling food products including training of machine-learning algorithms to recognize unknown features. The operations of the method 1100 of FIG. 11 correspond to machine readable instructions that are executed by the device 106 and/or the computing device 126, and specifically the controller 120. In the illustrated example, the instructions represented by the blocks of FIG. 11 are stored at the memory 118 for example, as the application 150. The method 1100 of FIG. 11 is another way in which the controller 120 and/or the device 106 and/or the computing device 126 and/or the system 100, 700, 1000 may be configured, for example as compared to the method 200, the method 500 and the method 800. Indeed, the methods 200, 500, 800, and 1100 may respectively represent a first, second, third and fourth modes in which the controller 120 and/or the device 106 and/or the computing device 126 and/or the systems 100, 700, 1000 may operate. Furthermore, the following discussion of the method 1100 of FIG. 11 will lead to a further understanding of the system 1000 (and/or the system 100, and/or other systems described herein) and its various components.

The method 1100 of FIG. 11 need not be performed in the exact sequence as shown and likewise various blocks may be performed in parallel rather than in sequence. Accordingly, the elements of method 1100 are referred to herein as "blocks" rather than "steps." The method 1100 of FIG. 11 may be implemented on variations of the system 1000, as well. Indeed, the method 1100 represents the example depicted in FIG. 10.

At a block 1102, the controller 120 receives, from the sensing device 1005, the respective sensed data 1012 of the food products 101 for (e.g. each of) the plurality of segments 1013 of the line 1014. As described above, the sensing device 1005 may comprise the line-scan dispersive spectrometer 105, and hence the respective sensed data 1012 may comprise respective spectra 112 of the food products 101 for (e.g. each of) the plurality of segments 1013.

However, the sensing device 1005 may comprise any suitable sensing device including, but not limited to, a line-scan camera, a line-scan x-ray device, a line-scan MRI device, and the like, with the sensed data 1012 adapted accordingly.

The block 1102 is otherwise similar to the block 202 of the method 200.

At a block 1104, the controller 120 applies the one or more machine learning algorithms 119 to the sensed data 1012 to classify the plurality of segments 1013 according to at least one of one or more food parameters. Indeed, the block 1104 is similar to the block 204 of the method 200. In some examples, the plurality of segments 1013 may be classified on a segment-by-segment basis. In other examples, groups of the plurality of segments 1013 may be classified.

At a block 1106, the controller 120 identifies, from the respective sensed data 1012, an unknown feature (e.g. the unknown feature 1015) not recognized by the one or more machine learning algorithms 119. For example, when the sensing device 1005 comprises the line-scan dispersive spectrometer 105 and the respective sensed data 1012 comprises the respective spectra 112, the controller 120 may be configured to identify the unknown feature by: detecting an unknown spectral feature in the respective spectra 112.

However, when the sensing device 1005 comprises a line-scan camera, the respective sensed data 1012 may comprise line-scan images, and the controller 120 may be configured to identify the unknown feature by: detecting an unknown image feature in the line-scan images. Similarly, when the sensing device 1005 comprises a line-scan x-ray device, the respective sensed data 1012 may comprise line-scan x-ray images, and the controller 120 may be configured to identify the unknown feature by: detecting an unknown x-ray image feature (e.g. an unknown shading and/or density) in the line-scan x-ray images. Similarly, when the sensing device 1005 comprises a line-scan MRI device, the respective sensed data 1012 may comprise line-scan MRI images, and the controller 120 may be configured to identify the unknown feature by: detecting an unknown MRI image feature (e.g. an unknown water density) in the line-scan MRI images.

At a block 1108, the controller 120 controls one or more of the sorting device 107 and the labeling device 109 to cause one or more of sorting and labeling of a respective food product 101 at which the unknown feature was detected. Hence, as described above, a respective food product 101 may be sorted from other food products, and transferred for analysis and/or further investigation by the user 602 and/or the at least one measurement device 603.

At a block 1110, the controller 120 receives, via one or more of the communication interface 122 and the input device 124, feedback 1043 to classify the unknown feature as a learned feature. As described above, the feedback 1043 may comprise one or more of: expert feedback, comprising a machine learning classifier of the learned feature, a specific identification of a food impurity, a chemical identification and/or composition of a food impurity, and the like.

In some examples, the feedback 1043 may comprise one or more of: a chemical identification and/or composition of a food product 101, a pH of a food product 101, and a water holding capacity of a food product 101, and the like.

In other examples, the feedback 1043 may comprise one or more of: a physical measurement of a food product 101, a fat content of a food product 101, a protein content of a food product 101, a water content of a food product 101, a lean content of a food product 101, a tenderness of a food product 101, a juiciness of a food product, a color of a food product 101, an integrity measurement of a food product 101, a flavor of a food product 101, marbling of a food product 101, and the like.

Furthermore, it is understood that when the feedback 1043 is received via the communication interface 122, the feedback 1043 is received from the remote computing device 601, and when the feedback 1043 is received via the input device 124, the feedback 1043 is received locally via the input device 124.

Furthermore, the feedback 1043 may include expert feedback (e.g. the feedback 1031), machine learning classifiers and/or machine learning regressors of at least one of the one or more food parameters, measurement feedback 1033 of the at least one measurement device 603, and the like.

At a block 1112, the controller 120 updates the one or more machine learning algorithms 119 to classify the plurality of segments 1013 according to the learned feature such that respective segments of further sensed data 1012 of further food products 101 are classified according to one or more of the learned features and at least one of the one or more food parameters. For example, a new classifier 1060 and/or a new regressor 1061 may be generated (and/or received) which is used to classify the plurality of segments 1013 according to the learned feature.

Other types of training the one or more machine learning algorithms 119 are within the scope of present examples, and which may be specific to a type of sensing device.

Figure 12:
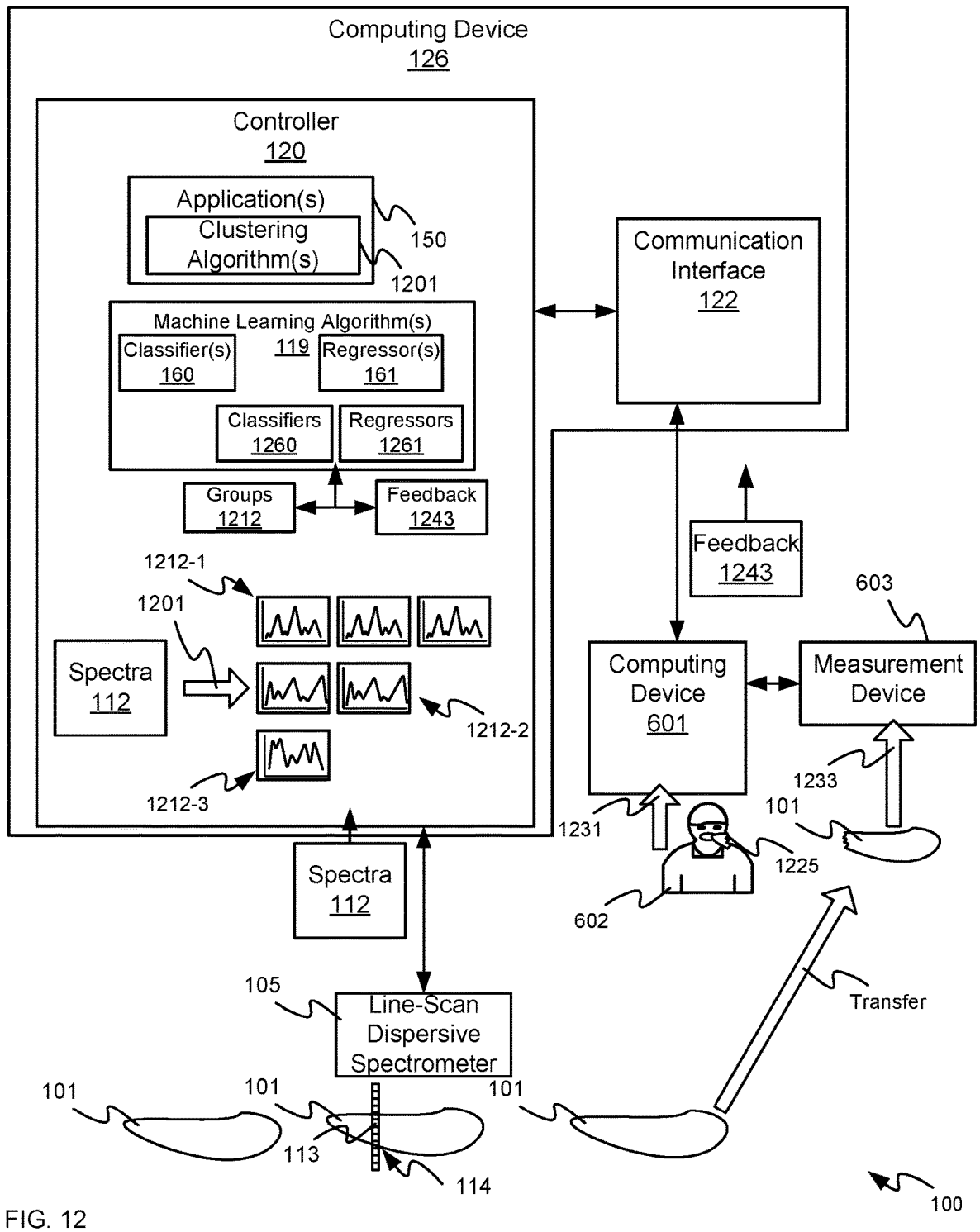
FIG. 12 depicts a portion of the system of FIG. 1 in a training mode that uses clustering algorithms, in accordance with some examples.

For example, attention is next directed to FIG. 12 which again depicts the system 100 (e.g. as depicted in FIG. 6 but with the sorting device 107) in another training mode in which at least one clustering algorithm 1201 (referred to interchangeably hereafter as the clustering algorithm 1201) may be used to train the one or more machine learning algorithms 119. As depicted, the clustering algorithm 1201 may be a component of the application 150; however, the clustering algorithm 1201 may be stored at the memory 118 independent of the application 150. In general, the clustering algorithm 1201 may be used to group one or more of the respective spectra 112 and spectral features of the respective spectra 112 into a plurality of groups, which may be used to train the one or more machine learning algorithms 119 in conjunction with feedback received from the computing device 601.

In these examples, the controller 120 may be configured to: receive, from the at least one line-scan dispersive spectrometer 105, the respective spectra 112 of the food products 101 for (e.g. each of) the plurality of segments 113 of the line 114; apply the clustering algorithm 1201 to group one or more of the respective spectra 112 and spectral features of the respective spectra 112 into a plurality of groups; receive, via one or more of the communication interface 122 and the input device 124, feedback to classify the plurality of groups according to one or more food parameters (which may include, but is not limited to, time-distant events); update the one or more machine learning algorithms 119 to classify the plurality of segments 113 according to the feedback such that respective segments 113 associated with further respective spectra 112 of further food products 101 are classified according to at least one of the one or more food parameters.

For example, as depicted, the spectra 112 acquired for the segments 113 (e.g. for the depicted food products 101) is received at the controller 120; and the controller 120 uses the clustering algorithm 1201 to group the spectra 112 into a plurality of groups 1212-1, 1212-2, 1212-3 (interchangeably referred to hereafter, collectively, as the groups 1212 and, generically, as a group 1212). While three groups 1212 are depicted, the controller 120 may classify the spectra 112 into any suitable number of groups 1212. the groups 1212 (e.g. each of the groups 1212) include similar and/or the same respective spectral features.

Furthermore, while, as depicted, (e.g. each of) the groups 1212 include entire respective spectra 112, in other examples one or more of the groups 1212 may include subsets of the spectra 112, for example, specific spectral features of the spectra 112 (e.g. peaks that consistently appear at given wavelengths, and the like).

Furthermore, the controller 120 is generally configured to correlate the spectra 112 with segments 113 from which the spectra 112 were obtained, as well as with the food products 101 from which the spectra 112 were obtained. Hence, for example, for each spectra 112 of each group 1212, the controller 120 is configured to determine a segment 113 of the line 114 from which the spectra 112 were obtained and the food product 101 that was being analyzed when the spectra 112 were obtained.

As depicted, after the spectra 112 are obtained, the food products 101 are transferred to the facility where the user 602 and the at least one measurement device 603 are located, for further analysis.

In some examples (as depicted), while in a training mode, all the food products 101 being analyzed are transferred. In other examples (not depicted, but similar to FIG. 10), the controller 120 may be further configured to control one or more of the sorting device 107 and the labeling device 109 to one or more of sort and label the food products 101 according to the plurality of groups 1212 to cause the food products 101 to be transferred to the facility where the user 602 and/or the at least one measurement device 603 are located, such that the food products 101 are examined by one or more of the at least one measurement device 603 and an expert (e.g. the user 602) to provide feedback on the food products 101. In either example, (e.g. each of) the food products 101 transferred may be associated with an identifier to enable later correlation between feedback and the spectra 112 and/or the groups 1212.

The user 602 may taste and/or inspect a piece 1225 of each food product 101 received and/or the at least one measurement device 603 may be used to analyze and/or measure the food products food products 101, as described above, to respectively obtain feedback 1231 (similar to the feedback 621) and/or feedback 1233 (similar to the feedback 613) which may be transmitted as feedback 1243 (similar o feedback 623) to the controller 120 via the computing device 601 and the communication interface 122 (and/or received via the input device 124).

The feedback 1243 may be used, in conjunction with groups 1212 of the particular food product 101 from which the respective spectra 112 was obtained, to train and/or update the one or more machine learning algorithms 119 to classify the plurality of segments 113 according to the feedback 1243 such that respective segments 113 associated with further respective spectra 112 of further food products 101 are classified according to at least one of the one or more food parameters.

For example, (e.g. each of) the groups 1212 may be associated with different food parameters according to the feedback 1243. In one example, when the food products 101 are meat, the group 1212-1 may correspond to protein, the group 1212-2 may correspond to fat, and the group 1212-3 may correspond to bones.

Indeed, new classifiers 1260 and/or new regressors 1261 may be generated from the combination of the groups 1212 and the feedback 1243, the new classifiers 1260 and/or the new regressors 1261 for use by the one or more machine learning algorithms 119 in classifying the spectra 112 according to the feedback 1243. Thereafter, respective segments 113 associated with further spectra 112 of further food products 101 may be classified according to at least one of the one or more food parameters as represented by the classifiers 1260 and/or the regressors 1261, and/or any existing classifiers 160 and/or regressors 161.

Figure 13:
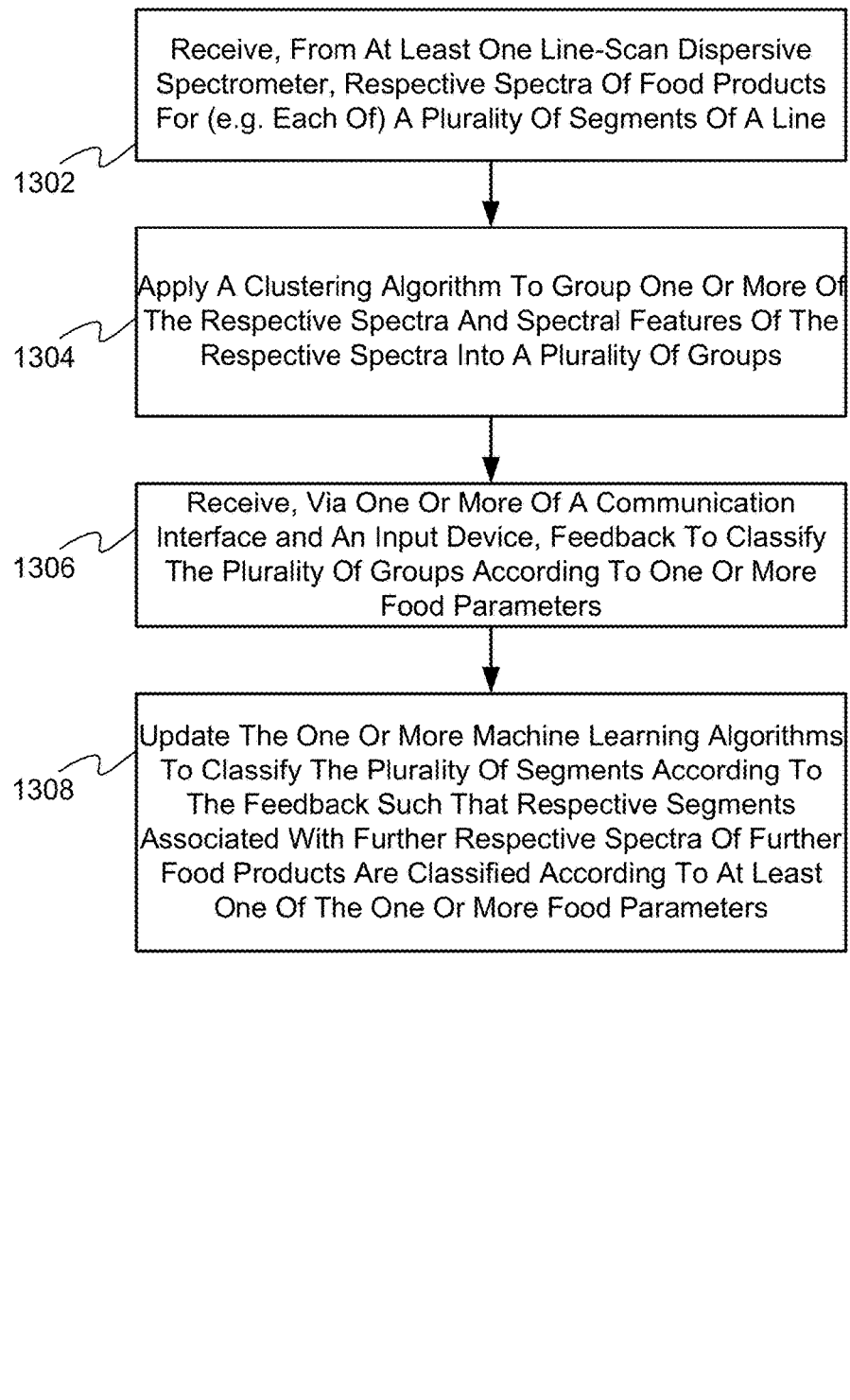
FIG. 13 is a flowchart of a method for one or more of sorting and labeling food products including training of machine-learning algorithms to recognize unknown features using clustering algorithms, in accordance with some examples.

Attention is now directed to FIG. 13 which depicts a flowchart representative of a method 1300 for one or more of sorting and labeling food products including training of machine-learning algorithms to recognize unknown features using clustering algorithms. The operations of the method 1300 of FIG. 13 correspond to machine readable instructions that are executed by the device 106 and/or the computing device 126, and specifically the controller 120. In the illustrated example, the instructions represented by the blocks of FIG. 13 are stored at the memory 118 for example, as the application 150. The method 1300 of FIG. 13 is another way in which the controller 120 and/or the device 106 and/or the computing device 126 and/or the systems 100, 700, system 1000 may be configured, for example as compared to the method 200, the method 500, the method 800 and the method 1100. Indeed, the methods 200, 500, 800, 1100 and 1300 may respectively represent a first, second, third, fourth and fifth modes in which the controller 120 and/or the device 106 and/or the computing device 126 and/or the systems 100, 700, 1000 may operate. Furthermore, the following discussion of the method 1300 of FIG. 13 will lead to a further understanding of the system 100 and its various components.

The method 1300 of FIG. 13 need not be performed in the exact sequence as shown and likewise various blocks may be performed in parallel rather than in sequence. Accordingly, the elements of method 1300 are referred to herein as "blocks" rather than "steps." The method 1300 of FIG. 13 may be implemented on variations of the system 100, as well. Indeed, the method 1300 represents the example depicted in FIG. 12.

At a block 1302, the controller 120 receives, from the at least one line-scan dispersive spectrometer 105, the respective spectra 112 of the food products 101 for (e.g. each of) the plurality of segments 113 of the line 114.

At a block 1304, the controller 120 applies the clustering algorithm 1201 to group one or more of the respective spectra 112 and spectral features of the respective spectra 112 into a plurality of groups.

In some examples, the block 1304 may include the controller 120 controlling one or more of the sorting device 107 and the labeling device 109 (e.g. via commands similar to the commands 1017) to one or more of sort and label the food products 101 according to the plurality of groups 1212 such that the food products 101 are examined by one or more of the at least measurement device 603 and an expert (e.g. the user 602) to provide the feedback 1243.

At a block 1306, the controller 120 receives, via the communication interface 122, the feedback 1243 to classify the plurality of groups according to one or more food parameters (which may include, but is not limited to, time-distant events).

In some examples, the feedback 1243 may comprise one or more of: a chemical identification and/or composition of a food product 101, a pH of a food product 101, a water holding capacity of a food product 101, and the like.

In other examples, the feedback 1243 may comprise one or more of: a physical measurement of a food product 101, a fat content of a food product 101, a protein content of a food product 101, a water content of a food product 101, a lean content of a food product 101, a tenderness of a food product 101, a juiciness of a food product, a color of a food product 101, an integrity measurement of a food product 101, a flavor of a food product 101, marbling of a food product 101, and the like.

Furthermore, the feedback 1243 may include expert feedback (e.g. the feedback 1231), machine learning classifiers and/or machine learning regressors of at least one of the one or more food parameters, measurement feedback 1233 of the at least one measurement device 603, and the like.

Furthermore, it is understood that when the feedback 1243 is received via the communication interface 122, the feedback 1243 is received from the remote computing device 601, and when the feedback 1243 is received via the input device 124, the feedback 1243 is received locally via the input device 124.

At a block 1308, the controller 120 updates the one or more machine learning algorithms 119 to classify the plurality of segments 113 according to the feedback 1243 such that respective segments 113 associated with further respective spectra 112 of further food products 101 are classified according to at least one of the one or more food parameters.

The method 1300 may be adapted for use with any suitable sensing device. For example, rather than the spectra 112, the controller 120 may receive and group sensed data (received from a sensing device, as described above) of the food products 101 for (e.g. each of) a plurality of segments of a line, and receive feedback to classify a plurality of groups of the sensed data according to one or more food parameters. Hence, in these examples, any suitable clustering algorithm may be used for any suitable type of sensed data. For example, when the system 100 includes a line-scan camera, clustering algorithms for grouping line-scan images of segments of a line may be used to group the line-scan images, for example according to shading and/or features of the line-scan images.

In some examples, any of the systems 100, 700, 1000 may be one of a plurality of systems in which training of machine learning algorithms of the plurality of systems occurs at a server and/or cloud computing device.

Figure 14:
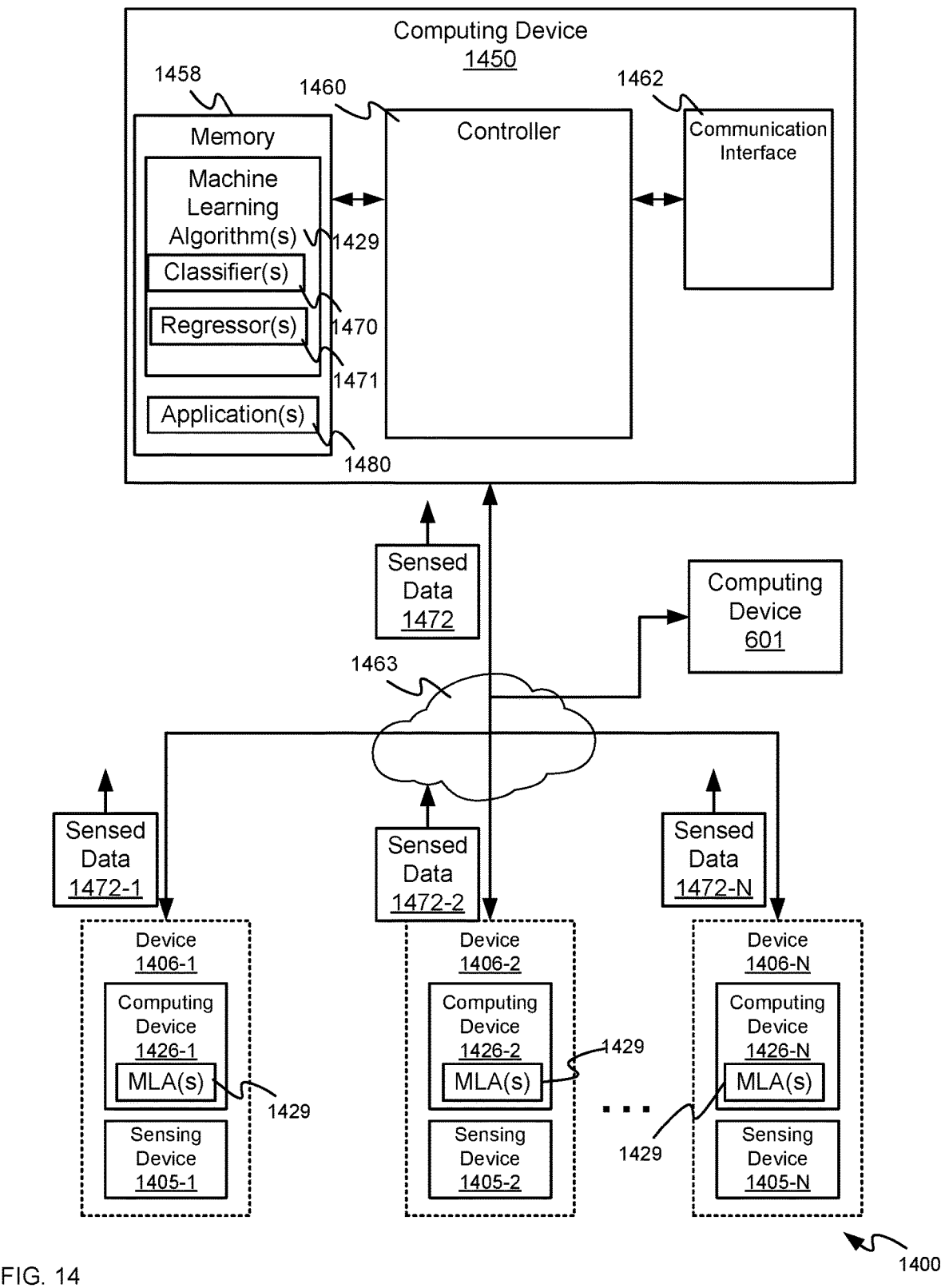
FIG. 14 depicts is a schematic view of a device and system for one or more of sorting and labeling food products using cloud-based training of machine-learning algorithms, in accordance with some alternative examples.

For example, attention is next directed to FIG. 14 which depicts a system 1400 that includes a plurality of sensing devices 1405-1, 1405-2 . . . 1405-N (interchangeably referred to hereafter, collectively, as the sensing devices 1405 and, generically, as a sensing device 1405), (e.g. each of) which may be a component of a respective device 1406-1, 1406-2 . . . 1406-N (interchangeably referred to hereafter, collectively, as the devices 1406 and, generically, as a 1406). Alternatively, a sensing device 1405 and/or a device 1406 may include a respective computing device 1426-1, 1426-2 . . . 1426-N (interchangeably referred to hereafter, collectively, as the computing devices 1426 and, generically, as a computing device 1426).

The sensing devices 1405, the devices 1406, and the computing devices 1426 may be respectively similar to the sensing devices 705, 1005 (and/or the line-scan dispersive spectrometer 105), the device 106, and the computing device 126. It is understood in FIG. 14 that the sensing devices 1405 are all of a same type. Hence, one or more respective machine learning algorithms 1429 may be used at (e.g. each of) the sensing devices 1405, the devices 1406, and/or the computing devices 1426 to classify similar food products (e.g. the food products 101) for sorting and/or labeling as described above. The one or more respective machine learning algorithms 1429 may be similar to, or the same as, the one or more machine learning algorithms 119 described above.

Indeed, each set of a sensing device 1405, a device 1406 and a computing device 1426 may be located at different locations, for example a separate food sorting facility, food labeling facility and/or food processing facility, for example to sort and/or label similar food products. However, in some instances, two sets of a sensing device 1405, a device 1406 and a computing device 1426 may be located at a same facility, but at different locations therein.

Furthermore, while an integer number "N" of sensing devices 1405, devices 1406 and computing devices 1426 are depicted, the system 1400 may comprise any suitable number of sensing devices 1405, and devices 1406 and/or computing devices 1426, with "N" being an integer value of at least 2. Hence, the system 1400 may generally comprise at least two sets of sensing device 1405, a device 1406 and a computing device 1426 and/or at least two food sorting locations and/or facilities, food labeling locations and/or facilities and/or food processing locations and/or facilities.

As depicted, the system 1400 further comprises the computing device 601 which provides expert feedback and/or measurement device feedback on food products, as described above. However, while only one computing device 601 is depicted, the system 1400 may comprise any number of similar computing devices 601, for example a computing device 601 for each set of a sensing device 1405, a device 1406 and a computing device 1426.

As depicted, the system 1400 further comprises a computing device 1450 which comprises a memory 1458, a controller 1460 and a communication interface 1462 which may be substantially similar, respectively, to the memory 118, the controller 120 and the communication interface 122 as described above, but adapted for the functionality of the computing device 1450, as described hereafter.

The computing device 1450 is generally in communication with the sensing devices 1405 (e.g. via one or more of a respective device 1406 and/or a respective computing device 1426) and the computing device 601 via a communication network 1463. As such the computing device 1450 may comprise one or more of a network-based server and/or a cloud computing device, and the like. Furthermore, while only one computing device 1450 is depicted, the functionality of the computing device 1450 may be located at two or more computing devices.

The memory 1458 of the computing device 1450 further stores copies of the one or more machine learning algorithms 1429, which include one or more classifiers 1470 and/or regressors 1471 of the similar food products being analyzed by the sensing devices 1405. As will be explained hereafter, training of the one or more machine learning algorithms 1429 may occur at the computing device 1450, and used to update the one or more machine learning algorithms 1429 at the sensing devices 1405. Indeed, while not depicted, (e.g. each of) the one or more machine learning algorithms 1429 at respective computing devices 1426 include the one or more classifiers 1470 and/or regressors 1471. The one or more classifiers 1470 and/or regressors 1471 may be similar to the classifiers 160 and/or regressors 161.

Functionality of the computing device 1450 will now be described.

In particular, the computing device 1450 comprises the communication interface 1462 which is configured to communicate with the plurality of sensing devices 1405 at a plurality of locations (e.g. different or same facilities), (e.g. each of) the plurality of sensing devices 1405 configured to acquire respective sensed data 1472-1, 1472-2, 1472-N of similar food products for a respective plurality of segments arranged along a respective line (e.g. as described throughout the present specification). As depicted, the sensed data 1472 is being transmitted to the computing device 1450 via the communication network 1463 and respective communication links.

Furthermore, while FIG. 14 depicts the computing device 1450 receiving the sensed data 1472 from all the sensing devices 1405, the computing device 1450 may receive the respective sensed data 1472 from only one of the sensing devices 1405.

Furthermore, not all respective sensed data 1472 generated using a respective sensing device 1405 may be transmitted. Rather, a subset of respective sensed data 1472 generated using a respective sensing device 1405 may be transmitted and/or the respective sensed data 1472 may be transmitted when unknown features are found in the respective sensed data 1472, as described above. In some examples, the respective sensed data 1472 is transmitted when a respective sensing device 1405 is in a training mode.

Furthermore, the respective sensed data 1472 may be transmitted to the computing device 1450 with identifiers of respective segments as well as identifiers of sensing devices 1405 from which the respective sensed data 1472 is received to enable the computing device 1450 to coordinate the respective sensed data 1472 with feedback as described below.

The computing device 1450 further comprises the memory 1458 storing the one or more machine learning algorithms 1429 trained to classify the respective sensed data 1472 of the respective plurality of segments into categories indicative of one or more food parameters, as described above. As depicted, the memory 1458 further stores at least one application 1480 which, when processed by the controller 1460, causes the controller 1460 to implement the functionality of the computing device 1450.

As depicted, the controller 1460 in communication with the communication interface 1462 and the memory 1458. In general, the controller 1460 is configured to: receive, via the communication interface 1462, from the plurality of sensing devices 1405, the respective sensed data 1472 of the similar food products for a respective plurality of segments; receive, via the communication interface 1462, feedback to classify the respective sensed data 1472 according to one or more of food parameters; further train the one or more machine learning algorithms 1429 to classify the respective plurality of segments according to the feedback and the respective sensed data 1472 to update at least one of: one or more of respective machine learning classifiers and respective machine learning regressors corresponding to at least one of the one or more food parameters; and the one or more machine learning algorithms; and provide, via the communication interface 1462, to one or more of the plurality of sensing devices 1405, the one or more of respective machine learning classifiers and the respective machine learning regressors to update respective machine learning algorithms 1429 at the one or more of the plurality of sensing devices 1405 such that respective segments of further respective sensed data of further food products are classified at the one or more of the plurality of sensing devices 1405 according to the at least one of the one or more food parameters.

Figure 15:
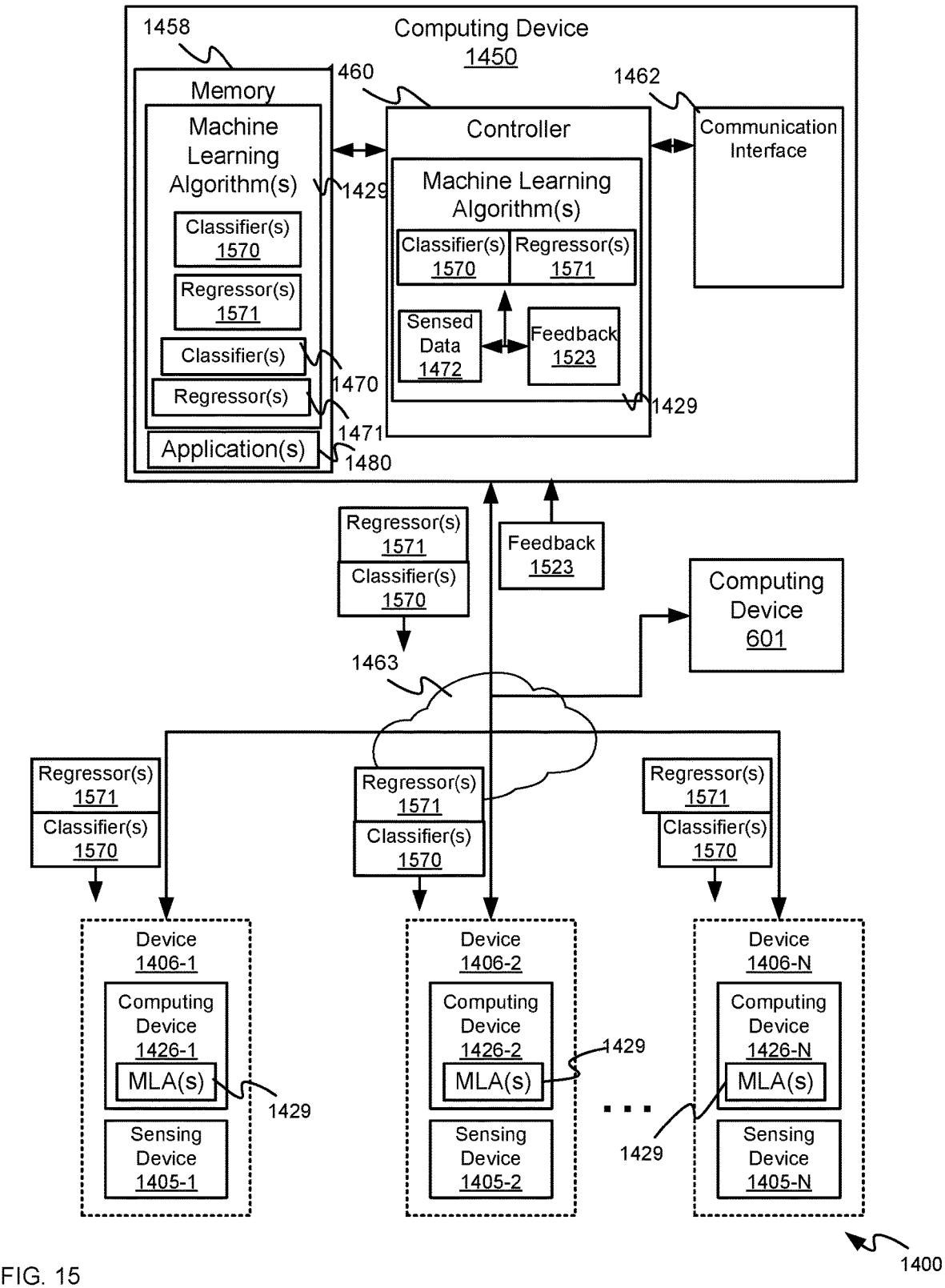
FIG. 15 depicts a cloud-based computing device of the system of FIG. 1 generating machine learning classifiers and/or machine learning regressors that are distributed to sensing devices of the system, in accordance with some examples.

For example, attention is next directed to FIG. 15 which depicts the system 1400 receiving feedback 1523 from the computing device 601. In particular, as described above, food products from which the sensed data 1472 was acquired, are transferred to the facility where the computing device 601 (and/or the user 602 and/or the at least one measuring device 603) are located and analyzed as described above. The feedback 1523 is generated (e.g. similar to the feedback 623, 1043, 1243) and transmitted to the computing device 1450.

At the computing device 1450, the controller 1460 further trains the one or more machine learning algorithms 1429 to classify the respective plurality of segments (e.g. analyzed by the sensing devices 1405) according to the feedback 1523 and the respective sensed data 1472, for example to generate one or more classifiers 1570 and/or regressors 1571 and/or update the classifiers 1470 and/or regressors 1471, as described above. The classifiers 1570 (and/or updated classifiers 1470) and/or regressors 1571 (and/or updated regressors 1571) are transmitted to the sensing devices 1405 such that the respective one or more machine learning algorithms 1429 at the sensing devices 1405 (and/or the devices 1406 and/or the computing devices 1426) may use the classifiers 1570 and/or regressors 1571 (and/or updated classifiers 1470 and/or updated regressors 1471) to sort and/or label similar food products.

Hence, sensed data 1472 from a sensing device 1405 at one location may be used to generate classifiers 1570 and/or regressors 1571 (and/or update classifiers 1470 and/or regressors 1471) at a sensing device 1405 at another location.

Figure 16:
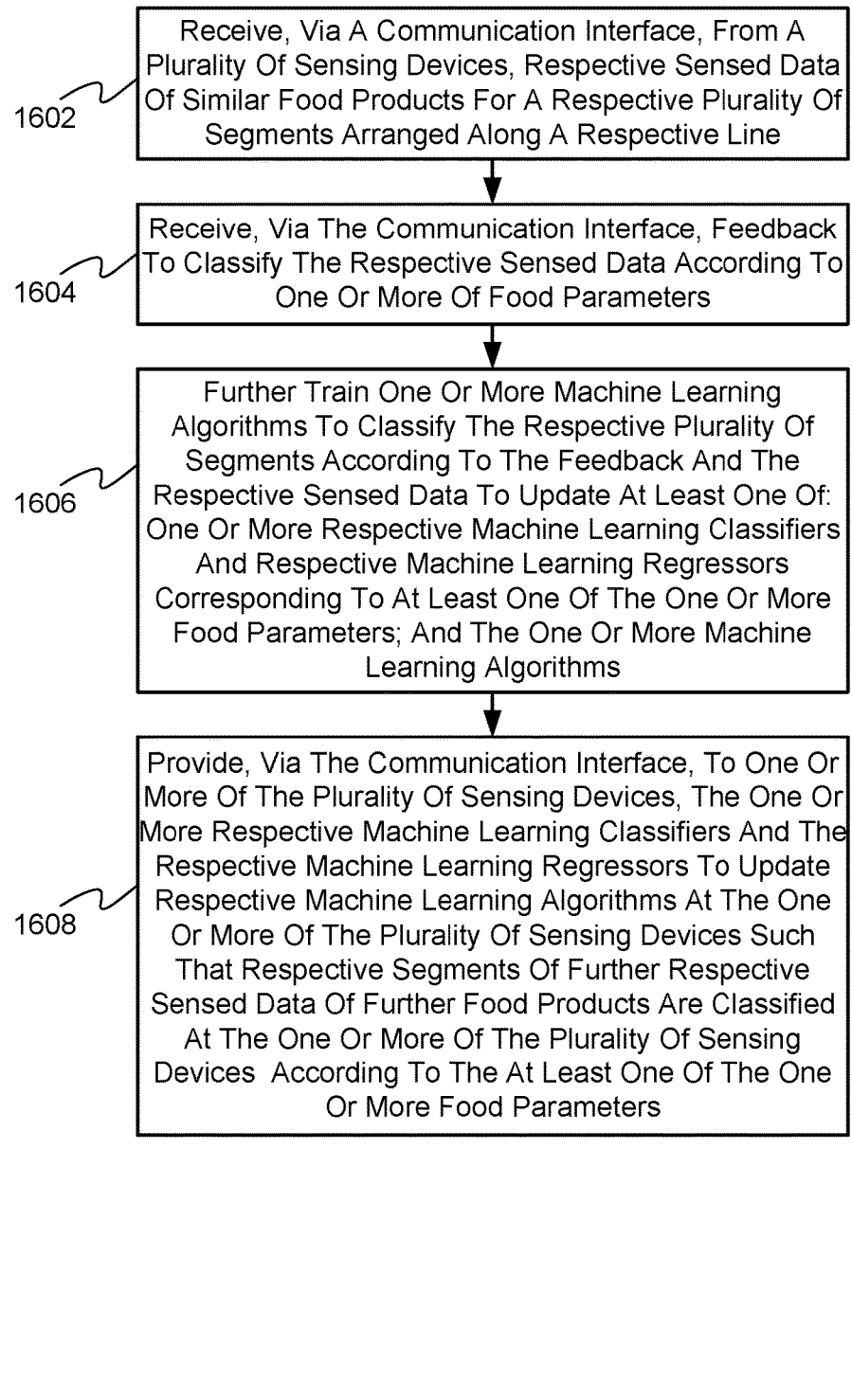
FIG. 16 is a flowchart of a method for one or more of sorting and labeling food products including cloud-based training of machine-learning algorithms, in accordance with some examples.

Attention is now directed to FIG. 16 which depicts a flowchart representative of a method 1600 for one or more of sorting and labeling food products including cloud-based training of machine-learning algorithms. The operations of the method 1600 of FIG. 16 correspond to machine readable instructions that are executed by the computing device 1450, and specifically the controller 1460. In the illustrated example, the instructions represented by the blocks of FIG. 16 are stored at the memory 1458 for example, as the application 1480. The method 1600 of FIG. 16 is one way in which the controller 1460 and/or computing device 1450 and/or the system 1400 and/or the systems 100, 700, 1000 may be configured. Indeed, the methods 200, 500, 800, 1100, 1300, 1600 may respectively represent a first, second, third, fourth, fifth and sixth modes in which the systems 100, 700, 1000, 1400 may operate. Furthermore, the following discussion of the method 1600 of FIG. 16 will lead to a further understanding of the system 1400, and its various components.

The method 1600 of FIG. 16 need not be performed in the exact sequence as shown and likewise various blocks may be performed in parallel rather than in sequence. Accordingly, the elements of method 1600 are referred to herein as "blocks" rather than "steps." The method 1600 of FIG. 16 may be implemented on variations of the system 1400 as well. Indeed, the method 1600 represents the examples depicted in FIG. 14 and FIG. 15.

At a block 1602, the controller 120 receives, via the communication interface 1462, from the plurality of sensing devices 1405, the respective sensed data 1472 of the similar food products for a respective plurality of segments along a respective line (e.g. respective segments of respective lines at the plurality of sensing devices 1405).

At a block 1604, the controller 120 receives, via the communication interface 1462, the feedback 1523 to classify the respective sensed data 1472 according to one or more of food parameters.

At a block 1606, the controller 120 further trains the one or more machine learning algorithms 1429 to classify the respective plurality of segments according to the feedback and the respective sensed data 1472 to update at least one of: respective machine learning classifiers 1470, 1570 and/or respective machine learning regressors 1471. 1571 corresponding to at least one of the one or more food parameters; and the one or more machine learning algorithms 1429.

At a block 1608, the controller 120 provides, via the communication interface 1462, to one or more of the plurality of sensing devices 1405, the respective machine learning classifiers 1470, 1570 and/or respective machine learning regressors 1471. 1571 to update respective machine learning algorithms 1429 at the one or more of the plurality of sensing devices 1405 such that respective segments of further respective sensed data of further food products are classified at the one or more of the plurality of sensing devices 1405 according to the at least one of the one or more food parameters.

Hence, provided herein are devices, systems and methods for sorting and labeling food products, for example using line-scan sensing devices, and which include training and/or cross-training of machine learning algorithms for recognizing features in sensed data from the line-scan sensing devices. While particular features of devices, systems and methods are described with respect to particular combinations of line-scan sensing devices, any of the features of a given device, system and/or method described herein may be adapted for use with any other suitable device, system and/or method and described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, XZ, and the like). Similar logic may be applied for two or more items in any occurrence of "at least one . . . " and "one or more . . . " language.

The terms "about", "substantially", "essentially", "approximately", and the like, are defined as being "close to", for example as understood by persons of skill in the art. In some examples, the terms are understood to be "within 10%," in other examples, "within 5%", in yet further examples, "within 1%", and in yet further examples "within 0.5%".

Persons skilled in the art will appreciate that in some examples, the functionality of devices and/or methods and/or processes described herein may be implemented using pre-programmed hardware or firmware elements (e.g., application specific integrated circuits (ASICs), electrically erasable programmable read-only memories (EEPROMs), etc.), or other related components. In other examples, the functionality of the devices and/or methods and/or processes described herein may be achieved using a computing apparatus that has access to a code memory (not shown) which stores computer-readable program code for operation of the computing apparatus. The computer-readable program code could be stored on a computer readable storage medium which is fixed, tangible and readable directly by these components, (e.g., removable diskette, CD-ROM, ROM, fixed disk, USB drive, solid state drive). Furthermore, it is appreciated that the computer-readable program may be stored as a computer program product comprising a computer usable medium. Further, a persistent storage device may comprise the computer readable program code. It is yet further appreciated that the computer-readable program code and/or computer usable medium may comprise a non-transitory computer-readable program code and/or non-transitory computer usable medium. Alternatively, the computer-readable program code could be stored remotely but transmittable to these components via a modem or other interface device connected to a network (including, without limitation, the Internet) over a transmission medium. The transmission medium may be either a non-mobile medium (e.g., optical and/or digital and/or analog communications lines) or a mobile medium (e.g., microwave, infrared, free-space optical or other transmission schemes) or a combination thereof.

Persons skilled in the art will appreciate that there are yet more alternative examples and modifications possible, and that the above examples are only illustrations of one or more examples. The scope, therefore, is only to be limited by the claims appended hereto.

What is claimed is:

1. A device for one or more of sorting and labelling food products, the device comprising:
   a first sensing device configured to acquire first sensed data of the food products for each of a plurality of first segments of a common sensed line;
   a second sensing device configured to acquire second sensed data of the food products for each of a plurality of second segments of the common sensed line;
   the first sensing device or the second sensing device comprising at least one line-scan dispersive spectrometer, and corresponding sensed data comprising respective spectra of the food products;
   a memory storing one or more machine learning algorithms initially trained to classify the first sensed data of the plurality of first segments into categories indicative of one or more food parameters; and
   a controller in communication with first sensing device, the second sensing device, the memory and one or more of a sorting device and a labelling device, the controller configured to:
   receive, from the first sensing device and the second sensing device respectively, the first sensed data and the second sensed data of the common sensed line;
   apply the one or more machine learning algorithms to the first sensed data to classify the plurality of first segments according to at least one of the one or more food parameters on a segment-by-segment basis;
   classify the plurality of second segments according to at least one of the one or more food parameters based on classifications of corresponding first segments of the first sensed data;
   train the one or more machine learning algorithms to classify the plurality of second segments according to at least one of the one or more food parameters based on the second sensed data and respective classifications of the second segments as determined from the corresponding first segments associated with the first sensed data; and
   control one or more of the sorting device and the labelling device according to classifying one or more of the plurality of first segments and the plurality of second segments to cause the food products to be one or more of sorted and labelled according to the at least one of the one or more food parameters.

2. The device of claim 1, wherein the one or more machine learning algorithms include one or more of respective classifiers and respective regressors indicative of the one or more food parameters, wherein classifiers and regressors corresponding to the second sensing device are generated from: the first sensed data the second sensing data.

3. The device of claim 1, wherein the at least one line-scan dispersive spectrometer is arranged relative to a conveyor such that one or more of the plurality of first segments and the plurality of second segments of the common sensed line corresponds to between about 0.5 mm and about 5 mm along a corresponding line at the conveyor.

4. The device of claim 1, wherein the at least one line-scan dispersive spectrometer has a pixel resolution of at least 128 segments across the line.

5. The device of claim 1, wherein the at least one line-scan dispersive spectrometer includes sensors for detecting wavelengths and the at least one line-scan dispersive spectrometer has a spectral resolution of one or more of: at least 128 wavelengths; and less than or equal to about 10 nm between the sensors.

6. The device of claim 1, wherein the at least one line-scan dispersive spectrometer is further configured to acquire the respective spectra in a wavelength range of one or more of: about 250 nm to about 900 nm; about 350 nm to about 1050 nm; about 700 nm to about 2200 nm; about 900 nm to 1700 nm; about 900 nm to about 2500 nm; about 800 nm to about 1700 nm; about 350 nm to about 800 nm; about 350 nm to about 1700 nm; and about 250 nm to about 2700 nm.

7. The device of claim 1, wherein the at least one line-scan dispersive spectrometer is further configured to acquire the respective spectra in a plurality of wavelength ranges, which fall in range of between about 250 nm to about 2700 nm.

8. The device of claim 1, wherein the controller is further configured to:
preprocess at least a portion of the respective spectra using one or more spectral feature-finding algorithms to determine spectral features of the respective spectra, the spectral features including one or more of: respective locations of peaks of the respective spectra; respective magnitudes of the peaks of the respective spectra; relative magnitudes of the peaks of the respective spectra; relative widths of the peaks of the respective spectra; slopes of the peaks of the respective spectra; a first derivative of the respective spectra; a second derivative of the respective spectra; spectral peak overlaps of the respective spectra; and valleys between the peaks of the respective spectra; other spectral features; and
classify, using the one or more machine learning algorithms, a corresponding plurality of line segments according to the one or more food parameters based on the spectral features.

9. The device of claim 1, wherein the controller is further configured to:
preprocess at least a portion of the respective spectra by comparing at least a portion of the respective spectra to a standard spectra.

10. The device of claim 1, wherein the controller is further configured to:
determine when a given sensor of the at least one line-scan dispersive spectrometer is one or more of noisy and biased to a given state; and, in response,
correct a given respective spectra determined using the given sensor, prior to applying the one or more machine learning algorithms, using interpolation between respective signals of neighbor sensors of the given sensor.

11. The device of claim 1, wherein the controller is further configured to:
when the respective spectra for a given classification drifts over time, control one or more of the sorting device, the labelling device and a notification device to provide a notification to cause a calibration of the at least one line-scan dispersive spectrometer.

12. A method for one or more of sorting and labelling food products, the method comprising:
receiving, at a controller, from a first sensing device a ad a second sensing device respectively, first sensed data and second sensed data of common sensed line, the first sensing device configured to acquire the first sensed data of the food products for each of a plurality of first segments of the commons sensed line, the second sensing device configured to acquire the second sensed data of the food products for each of a plurality of second segments of the common sensed line, the first sensing device or the second sensing device comprising at least one line-scan dispersive spectrometer, and corresponding sensed data comprising respective spectra of the food products;
applying, at the controller, one or more machine learning algorithms to the first sensed data to classify the plurality of first segments according to at least one of one or more food parameters on a segment-by-segment basis, the one or more machine learning algorithms initially trained to classify the first sensed data of the plurality of first segments into categories indicative of the one or more food parameters;
classifying, at the controller, the plurality of second segments according to at least one of the one or more food parameters based on classifications of corresponding first segments of the first sensed data;
training the one or more machine learning algorithms to classify the plurality of second segments according to at least one of the one or more food parameters based on the second sensed data and respective classifications of the second segments as determined from the corresponding first segments associated with the first sensed data; and
controlling, at the controller, one or more of a sorting device and a labelling device according to classifying one or more of the plurality of first segments and the plurality of second segments to cause the food products to be one or more of sorted and labelled according to the at least one of the one or more food parameters.

13. The method of claim 12, wherein the one or more machine learning algorithms include one or more of respective classifiers and respective regressors indicative of the one or more food parameters, wherein classifiers and regressors corresponding to the second sensing device are generated from the first sensed data, the second sensed data, and corresponding classifiers and corresponding associated with the first sensing device.

14. The method of claim 12, wherein the at least one line-scan dispersive spectrometer is arranged relative to a conveyor such that one or more of the plurality of first segments and the plurality of segment segments of the common sensed line corresponds to between about 0.5 mm and about 5 mm along a corresponding line at the conveyor.

15. The method of claim 12, wherein the at least one line-scan dispersive spectrometer includes sensors for detecting wavelengths, and the at least one line-scan dispersive spectrometer has a spectral resolution of one or more of: at least 128 wavelengths; and less than or equal to about 10 nm between the sensors.

16. The method of claim 12, wherein the at least one line-scan dispersive spectrometer is further configured to acquire the respective spectra in a plurality of wavelength ranges, which fall in range of between about 250 nm to about 2700 nm.

17. The method of claim 12, further comprising:
preprocessing at least a portion of the respective spectra using one or more spectral feature-finding algorithms to determine spectral features of the respective spectra, the spectral features including one or more of: respective locations of peaks of the respective spectra; respective magnitudes of the peaks of the respective spectra; relative magnitudes of the peaks of the respective spectra; relative widths of the peaks of the respective spectra; slopes of the peaks of the respective spectra; a first derivative of the respective spectra; a second derivative of the respective spectra; spectral peak overlaps of the respective spectra; and valleys between the peaks of the respective spectra; other spectral features; and classifying, using the one or more machine learning algorithms, a corresponding plurality of line segments according to the one or more food parameters based on the spectral features.

18. The method of claim 12, further comprising:

preprocessing at least a portion of the respective spectra by comparing at least a portion of the respective spectra to a standard spectra.

19. The method of claim 12, further comprising:

determining when a given sensor of the at least one line-scan dispersive spectrometer is one or more of noisy and biased to a given state; and, in response, correcting a given respective spectra determined using the given sensor, prior to applying the one or more machine learning algorithms, using interpolation between respective signals of neighbor sensors of the given sensor.

20. The method of claim 12, further comprising:

when the respective spectra for a given classification drifts over time, controlling one or more of the sorting device, the labelling device and a notification device to provide a notification to cause a calibration of the at least one line-scan dispersive spectrometer.

\* \* \* \* \*